US012624022B2

(12) United States Patent
McGowan et al.

(10) Patent No.: US 12,624,022 B2
(45) Date of Patent: May 12, 2026

(54) HETEROCYCLIC IMMUNOMODULATORS AS PDL1 CHECKPOINT INHIBITOR

(71) Applicant: Janssen Sciences Ireland Unlimited Company, County Cork (IE)

(72) Inventors: David Craig McGowan, Beerse (BE); Edgar Jacoby, Beerse (BE)

(73) Assignee: JANSSEN SCIENCES IRELAND UNLIMITED COMPANY, County Cork (IE)

( * ) Notice: Subject to any disclaimer, the term of this patent is extended or adjusted under 35 U.S.C. 154(b) by 1191 days.

(21) Appl. No.: 17/595,711

(22) PCT Filed: Jun. 5, 2020

(86) PCT No.: PCT/EP2020/065646
§ 371 (c)(1),
(2) Date: Nov. 23, 2021

(87) PCT Pub. No.: WO2020/245372
PCT Pub. Date: Dec. 10, 2020

(65) Prior Publication Data

US 2022/0259186 A1 Aug. 18, 2022

(30) Foreign Application Priority Data

Jun. 7, 2019 (EP) .................................... 19179072

(51) Int. Cl.
*C07D 405/14* (2006.01)
*C07D 405/04* (2006.01)
*C07D 405/12* (2006.01)

(52) U.S. Cl.
CPC ......... *C07D 405/14* (2013.01); *C07D 405/04* (2013.01); *C07D 405/12* (2013.01)

(58) Field of Classification Search
CPC ... C07D 405/14; C07D 405/04; C07D 405/12
See application file for complete search history.

(56) References Cited

FOREIGN PATENT DOCUMENTS

| | | | |
|---|---|---|---|
| JP | 2006104062 | A | 4/2006 |
| WO | 2018005374 | A1 | 1/2018 |
| WO | 2018009505 | A1 | 1/2018 |
| WO | 2018183171 | A1 | 10/2018 |

OTHER PUBLICATIONS

Zak, K., Grudnik, P., Magiera, K., Domling, A., Dubin, G., Holak, T.; Structural Biology of the Immune Checkpoint Receptor PD-1 and Its Ligands PD-L1/PD-L2. Structure; Aug. 1, 2017; 25(8): 1163-1174 (Year: 2017).*

Xu-Monette, Z., Zhang, M., Jianyong, L., Young, K.; PD-1/PD-L1 Blockade: Have We Found the Key to Unleash the Antitumor Immune Response?. Frontiers in Immunology; Dec. 3, 2017; vol. 8; Article 1597 (Year: 2017).*

Wykes, M., Lewin, S.; Immune checkpoint blockade in infectious diseases. Nature Reviews Immunology; Oct. 9, 2017; 18, 91-104 (Year: 2018).*

De Sousa Linhares, A., Leitner, J., Grabmeier-Pfistershammer, K., Steinberger, P.; Not All Immune Checkpoints Are Created Equal. Frontiers in Immunology; Aug. 30, 2018; vol. 9; Article 1909 (Year: 2018) (Year: 2018).*

International Search Report issued Jul. 31, 2020 in PCT/EP2020/065646.

Written Opinion issued Jul. 31, 2020 in PCT/EP2020/065646.

Brown, J.A., et al, "Blockade of Programmed Death-1 Ligands on Dendritic Cells Enhances T Cell Activation and Cytokine Production," J. Immunol, vol. 170, pp. 1257-1266, 2003.

Dong, H., et al, "Tumor-associated B7-H1 promotes T-cell apoptosis: A potential mechanism of immune evasion," Nature Medicine, vol. 8, No. 8, pp. 793-800, Aug. 2002.

Hamanishi, J., et al, "Programmed cell death 1 ligand 1 and tumor-infiltrating CD8+ T lymphocytes are prognostic factors of human ovarian cancer," PNAS, vol. 104, No. 9, pp. 3360-3365, Feb. 27, 2007.

Strome, S.E., et al, "B7-H1 Blockade Augments Adoptive T-Cell Immunotherapy for Squamous Cell Carcinoma," Cancer Research, vol. 63, pp. 6501-6505, Oct. 1, 2003.

Inman, B.A., et al, "PD-L1 (B7-H1) Expression by Urothelial Carcinoma of the Bladder and BCG-Induced Granulomata," Cancer, vol. 109, No. 8, pp. 1499-1505, Apr. 15, 2007.

Konishi, J., et al, "B7-H1 Expression on Non-Small Cell Lung Cancer Cells and Its Relationship with Tumor-Infiltrating Lymphocytes and Their PD-1 Expression," Clinical Cancer Research, vol. 10, pp. 5094-5100, Aug. 1, 2004.

Nakanishi, J., et al, "Overexpression of B7-H1 (PD-L1) significantly associates with tumor grade and postoperative prognosis in human urothelial cancers," Cancer Immunol Immunother, vol. 56, pp. 1173-1182, 2007.

(Continued)

*Primary Examiner* — Yih-Horng Shiao
*Assistant Examiner* — Christopher Lindsay Johnson
(74) *Attorney, Agent, or Firm* — Ice Miller LLP

(57) ABSTRACT

The disclosure describes pyridinone-containing inhibitors of PD-L1, pharmaceutical compositions comprising these compounds, chemical processes for preparing these compounds, and their use in the treatment of infectious diseases and cancer.

(I)

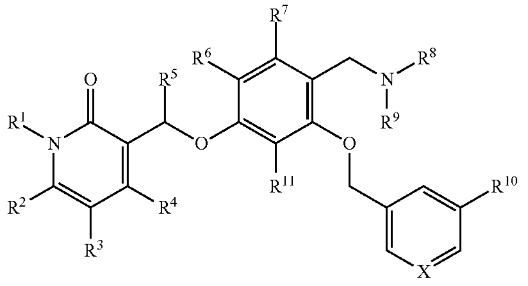

16 Claims, No Drawings

(56) References Cited

OTHER PUBLICATIONS

Tie, Y., et al, "Safety and efficacy of nivolumab in the treatment of cancers: A meta-analysis of 27 prospective clinical trials," International Journal of Cancer, vol. 140, pp. 948-958, 2016.
Dyson, G., et al, "Chemistry of Synthetic Drugs [in Russian]," translation from English, Moscow: "Mir", 1964, pp. 12-19.
Belikov, V.G., "Pharmaceutical chemistry [in Russian]" Textbook, Moscow: "MEDpress-inform," 2007, pp. 27-29.
Kummerer, K., "Pharmaceuticals in the environment," Annual Review of Environment and Resources, vol. 35, 2010, 2 pages.
Mashkovskiy M.D., "Medicaments [in Russian]," Moscow: "Novaya Volna", 2001, vol. 1, p. 11 (translation 2 pages).
Durnov, L.A., et al, "Pediatric oncology [in Russian]," Moscow: "Meditsina", 2002, p. 139 (translation 3 pages).

* cited by examiner

HETEROCYCLIC IMMUNOMODULATORS AS PDL1 CHECKPOINT INHIBITOR

CROSS REFERENCE TO RELATED APPLICATION

This application is a Section 371 of International Application No. PCT/EP2020/065646, filed on Jun. 5, 2020, which published in the English language on Dec. 10, 2020 under International Publication No. WO2020/245372 A1, which claims priority to EP Patent Application No. 19179072.4 filed on Jun. 7, 2019, the disclosures of which are incorporated herein by reference in their entireties.

BACKGROUND

Programmed death-ligand 1 (PD-L1) is a 40 kDa immune checkpoint protein encoded in humans by the CD274 gene. Upon binding to its receptor PD-1, which is expressed on activated B cells, T cells, and myeloid cells, PD-L1 initiates signaling pathways that lead to downregulation of T cell proliferation and activation, facilitating tumor cell escape from T cell-mediated immune surveillance, thereby contributing to cancer severity and progression. PD-L1 expression has been shown on a wide variety of solid tumors (e.g., breast, lung, colon, ovarian, melanoma, bladder, liver, salivary, stomach, gliomas, thyroid, thymic epithelial, head, and neck (Brown J A et al., 2003. J. Immunol. 170:1257-66; Dong H et al. 2002. Nat. Med. 8:793-800; Hamanishi J, et al. 2007. Proc. Natl. Acad. Sci. USA 104:3360-65; Strome S E et al. 2003. Cancer Res. 63:6501-5; Inman B A et al. 2007. Cancer 109:1499-505; Konishi J et al. 2004. Clin. Cancer Res. 10:5094-100; Nakanishi J et al. 2007. Cancer Immunol. Immunother. 56:1173-82)), and the protein has arisen as an attractive target for the development of anti-cancer therapeutics. PD-L1 expression is further involved in the evasion of immune responses involved in infectious diseases (e.g., chronic viral infections including HBV and HIV). As such, PD-L1 also serves as a therapeutic target for the treatment of a variety of infectious diseases.

Therapeutic efficacy of PD-L1 antagonists (and of PD-1 antagonists) has been validated in clinical trials. However, response rates remain low. For example, Opdivo® (Nivolumab) treatment achieved a 26% objective response rate (ORR) across the 27 clinical trials analyzed (Tie Y et al., 2016 Int. J. Cancer. 140:948-58). Accordingly, there is a need in the art for effective treatments for PD-L1-associated diseases.

SUMMARY

The present disclosure is directed to the general and preferred embodiments defined, respectively, by the independent and dependent claims appended hereto, which are incorporated by reference herein. In particular, the present disclosure is directed to compounds of Formula (I):

(I)

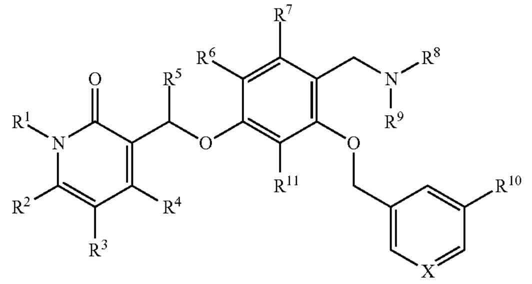

including the stereoisomers or tautomeric forms thereof, or a pharmaceutically acceptable salt thereof, wherein $R^1$ is a ring optionally substituted with one or more substituents selected from halogen, CN, $C_{1-6}$alkyl, $C_{1-6}$haloalkyl, $C_{3-6}$cycloalkyl, $C_{1-6}$heteroalkyl, $NR^xR^y$, $NR^xC(=O)R^y$, $NR^xCO_2R^y$, $NR^xC(=O)NR^xR^y$, $OC(=O)NR^xR^y$, O-(6 to 10-membered aryl), O-(5 to 10-membered heteroaryl), and a ring;

$R^2$, $R^3$, $R^4$, $R^5$, $R^6$, $R^7$ and $R^{11}$ are independently selected from H, halogen, $C_{1-4}$alkyl and $C_{1-4}$alkyl substituted with one or more F;

$R^8$ and $R^9$ are independently selected from H, $C_{1-6}$alkyl and $C_{1-6}$heteroalkyl, each of $C_{1-6}$alkyl and $C_{1-6}$heteroalkyl being optionally substituted with one or more substituents selected from $C_{1-4}$alkyl, OH, $OCH_3$, —$CO_2H$, —$CO_2C_{1-4}$alkyl, $C_{3-6}$heterocycle, aryl and heteroaryl;

wherein $C_{3-6}$heterocycle is optionally substituted with one or more substituent selected from oxo, OH and $CO_2H$;

with the proviso that $R^8$ and $R^9$ are not both H;

or wherein $R^8$ and $R^9$ are connected together to form a $C_{3-6}$heterocycle optionally substituted with one or more substituents selected from $C_{1-6}$alkyl, oxo, OH and $CO_2H$;

$R^{10}$ is selected from H, CN, halogen, $C_{1-6}$alkyl, $OC_{1-6}$alkyl, $C_{1-6}$alkyl-$CO_2H$, $C_{1-6}$alkyl-$CO_2$—$C_{1-6}$-alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl$)_2$, $C(=O)NR^xR^y$, $SO_2$—$C_{1-6}$alkyl, aryl and heteroaryl;

wherein aryl and heteroaryl are optionally substituted with one or more substituents selected from CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$ alkyl-C(O)$NH_2$, $C_{1-6}$alkyl-CO—$NHC_{1-6}$alkyl, $C_{1-6}$alkyl-C(O)N($C_{1-6}$alkyl$)_2$, $C(=O)NR^xR^y$ and $SO_2$—$C_{1-6}$ alkyl;

X is N or $CR^{12}$;

$R^{12}$ is selected from H, F, Cl, CN, $C(=O)NR^xR^y$, aryl and heteroaryl, wherein aryl and heteroaryl are optionally substituted with one or more substituents selected from CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl$)_2$, $C(=O)NR^xR^y$ and $SO_2$—$C_{1-6}$alkyl; and $R^x$ and $R^y$ are independently selected from H and $C_{1-6}$alkyl.

In embodiments, the compounds of Formula (I) are compounds selected from those species described or exemplified in the detailed description below.

The present disclosure is also directed to pharmaceutical compositions comprising a compound of Formula (I) or a pharmaceutically acceptable salt thereof. Pharmaceutical compositions may further comprise a pharmaceutically acceptable carrier.

The present disclosure is also directed to a pharmaceutical combination comprising a first compound and a second compound as a combined preparation for simultaneous, separate or sequential use in the prevention or treatment of an infection or cancer in a mammal in need thereof, wherein said first compound is different from said second compound. Pharmaceutical combinations may comprise a compound of Formula (I), a pharmaceutically acceptable salt thereof, or a pharmaceutical composition comprising a compound of Formula (I) and a pharmaceutically acceptable carrier. Pharmaceutical combinations may further comprise another ingredient active against said infection or cancer.

The present disclosure is also directed to a compound of Formula (I), a pharmaceutically acceptable salt thereof, or a pharmaceutical composition comprising a compound of Formula (I) and a pharmaceutically acceptable carrier for use as a medicament.

The present disclosure is also directed to a compound of Formula (I), a pharmaceutically acceptable salt thereof, or a pharmaceutical composition comprising a compound of Formula (I) and a pharmaceutically acceptable carrier for use in the prevention or treatment of an infectious disease, more particularly a bacterial, viral or fungal infectious disease, more particularly a viral infectious disease in a subject in need thereof.

The present disclosure is also directed to a compound of Formula (I), a pharmaceutically acceptable salt thereof, or a pharmaceutical composition comprising a compound of Formula (I) and a pharmaceutically acceptable carrier for use in the prevention or treatment of an HBV infection or of an HBV-induced disease in a subject in need thereof.

The present disclosure is also directed to a compound of Formula (I), a pharmaceutically acceptable salt thereof, or a pharmaceutical composition comprising a compound of Formula (I) and a pharmaceutically acceptable carrier for use in the prevention or treatment of chronic hepatitis B in a subject in need thereof.

The present disclosure is also directed to a compound of Formula (I), a pharmaceutically acceptable salt thereof, or a pharmaceutical composition comprising a compound of Formula (I) and a pharmaceutically acceptable carrier for use in the treatment of cancer, more particularly for inhibiting, growth, proliferation, or metastasis of cancer cells in a subject in need thereof.

The present disclosure is also directed to a compound of Formula (I), a pharmaceutically acceptable salt thereof, or a pharmaceutical composition comprising a compound of Formula (I) and a pharmaceutically acceptable carrier for use in a method for enhancing, stimulating, modulating, or increasing the immune response in a subject in need thereof.

The present disclosure is also directed to a compound of Formula (I), a pharmaceutically acceptable salt thereof, or a pharmaceutical composition comprising a compound of Formula (I) and a pharmaceutically acceptable carrier for use as an immune checkpoint inhibitor, more particularly as a PDL1 checkpoint inhibitor.

The present disclosure is also directed to a process for the preparation of a compound of Formula (I).

DETAILED DESCRIPTION

Provided herein are compounds of Formula (I):

(I)

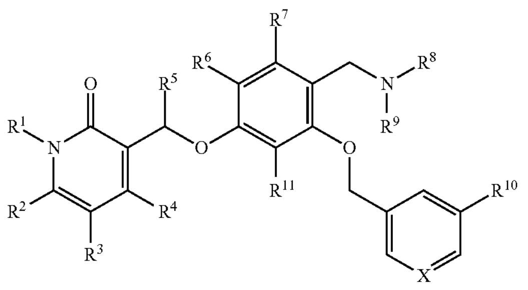

including the stereoisomers or tautomeric forms thereof, or a pharmaceutically acceptable salt thereof, useful in the inhibition of PD-1.

Definitions

Listed below are definitions of various terms used to describe the present disclosure. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the applicable art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include," "includes," and "included," is not limiting.

As used in the specification and in the claims, the term "comprising" can include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

All ranges disclosed herein are inclusive of the recited endpoint and independently combinable (for example, the range of "from 50 mg to 300 mg" is inclusive of the endpoints, 50 mg and 300 mg, and all the intermediate values). The endpoints of the ranges and any values disclosed herein are not limited to the precise range or value; they are sufficiently imprecise to include values approximating these ranges and/or values.

As used herein, approximating language can be applied to modify any quantitative representation that can vary without resulting in a change in the basic function to which it is related. Accordingly, a value modified by a term or terms, such as "substantially," cannot be limited to the precise value specified, in some cases. In at least some instances, the approximating language can correspond to the precision of an instrument for measuring the value.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_{1-4}$alkyl as used here refers to a straight- or branched-chain alkyl group having from 1 to 4 carbon atoms in the chain. The term $C_{1-6}$alkyl as used here refers to a straight- or branched-chain alkyl group having from 1 to 6 carbon atoms in the chain.

The terms "alkoxy," "alkylamino," and "alkylthio" are used in their conventional sense, and refer to those alkyl groups attached to the remainder of the molecule via an O atom, an amino group, or a S atom, respectively.

The term "heteroalkyl" refers to a stable straight or branched chain, consisting of the stated number of carbon atoms and from one to three heteroatoms selected from the group consisting of O, N and S. The heteroatoms may be placed at any interior position of the heteroalkyl group, including the position at which the alkyl group is attached to the remainder of the molecule.

The term "haloalkyl" is used in its conventional sense, and refers to an alkyl group, as defined herein, substituted with one or more halo substituents.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

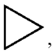, 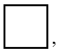, 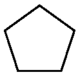, , 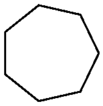 and 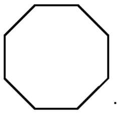.

The terms "heterocycle" and "heterocycloalkyl" refer to saturated or partially saturated monocyclic, fused polycyclic, or spiro polycyclic ring systems having 3 to 12 ring members and which contain carbon atoms and from 1 to 5 heteroatoms independently selected from the group consisting of N, O, and S. The terms "heterocycle" and "heterocycloalkyl" include cyclic esters (e.g., lactones) and cyclic amides (e.g., lactams). Examples of heterocycle and heterocycloalkyl groups include, but are not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, and benzo-1,4-dioxane. Unless otherwise noted, the heterocycle or heterocycloalkyl is attached to its pendant group at any heteroatom or carbon atom that results in a stable structure.

A monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel).

Particular examples of monocyclic, bicyclic or tricyclic aromatic carbocycles are phenyl, naphthyl, anthracenyl.

The term "phenyl" represents the following moiety:

.

The term "aryl," unless otherwise stated," refers to a polyunsaturated, typically aromatic, hydrocarbon group which can be a single ring or multiple rings (up to three rings) which are fused together or linked covalently. Examples of aryl groups include phenyl, naphthyl, anthracenyl.

The term "heteroaryl" refers to a monocyclic or bicyclic aryl ring system having 5 to 10 ring members and which contains carbon atoms and from 1 to 5 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5-membered rings, the heteroaryl ring preferably contains one member of nitrogen, oxygen or sulfur and, in addition, up to 3 additional nitrogens. In the case of 6-membered rings, the heteroaryl ring preferably contains from 1 to 3 nitrogen atoms. For the case wherein the 6-membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, oxazolyl, thiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

Those skilled in the art will recognize that the species of heteroaryl groups listed or illustrated above are not exhaustive, and that additional species within the scope of these defined terms may also be selected.

The term "cyano" refers to the group —CN.

The terms "halo" or "halogen" represent chloro, fluoro, bromo, or iodo.

The term "substituted" means that the specified group or moiety bears one or more substituents. The term "unsubstituted" means that the specified group bears no substituents.

The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p)

position across from the point of attachment. To further clarify the position of substituents on the phenyl ring, the 2 different ortho positions will be designated as ortho and ortho' and the 2 different meta positions as meta and meta' as illustrated below.

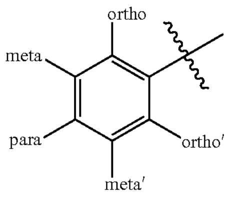

When referring to substituents on a pyridyl group, the terms "para", "meta", and "ortho" refer to the placement of a substituent relative to the point of attachment of the pyridyl ring. For example, the structure below is described as 3-pyridyl with the $X^1$ substituent in the ortho position, the $X^2$ substituent in the meta position, and $X^3$ substituent in the para position:

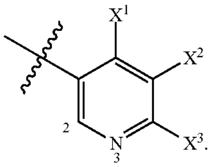

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

The compounds of this present disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enantiopure material that is of unknown configuration. In these cases (R*) or (S*) or (*R) or (*S) is used in the name to indicate that the absolute stereochemistry of the corresponding stereocenter is unknown. Thus, a compound designated as (R*) or (*R) refers to an enantiopure compound with an absolute configuration of either (R) or (S). In cases where the absolute stereochemistry has been confirmed, the structures are named using (R) and (S).

The symbols 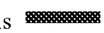 and 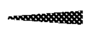 are used as meaning the same spatial arrangement in chemical structures shown herein. Analogously, the symbols 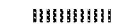 and 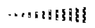 are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I), or pharmaceutically acceptable salts of compounds of Formula (I), may be obtained as solvates. Solvates include those formed from the interaction or complexation of compounds of the present disclosure with one or more solvents, either in solution or as a solid or crystalline form. In some embodiments, the solvent is water and the solvates are hydrates. In addition, certain crystalline forms of compounds of Formula (I), or pharmaceutically acceptable salts of compounds of Formula (I) may be obtained as co-crystals. In certain embodiments of the present disclosure, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, $R—COOH_{(s)}$, $R—COOH_{(sol)}$, and $R—COO^{-}_{(sol)}$. In this example, $R—COOH_{(s)}$ refers to the solid compound, as it could be for example in a tablet or some other solid pharmaceutical composition or preparation; $R—COOH_{(sol)}$ refers to the undissociated form of the compound in a solvent; and $R—COO^{-}_{(sol)}$ refers to the dissociated form of the compound in a solvent, such as the dissociated form of the compound in an aqueous environment, whether such dissociated form derives from R—COOH, from a salt thereof, or from any other entity that yields $R—COO^{-}$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as $R—COOH_{(aq)}$ and/or $R—COO^{-}_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^{+}H_3NCH_2COO^{-}$. Zwitterions, zwitterionic compounds, inner salts and dipolar ions in the known and well established meanings of these terms are within the scope of this present disclosure, as would in any case be so appreciated by those of ordinary skill in the art. Because there is no need to name each and every embodiment that would be recognized by those of ordinary skill in the art, no structures of the zwitterionic compounds that are associated with the compounds of this present disclosure are given explicitly herein. They are, however, part of the embodiments of this present disclosure. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorus, sulfur, fluorine, chlorine, and iodine such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example deuterium (i.e., D or $^{2}H$); or tritium (i.e., T or $^{3}H$)), detection or imaging techniques such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this present disclosure and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this present disclosure given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $G^1$, $G^2$, $G^3$, $G^4$, $G^5$, $G^6$, $G^7$, $G^8$, $G^9$, $G^{10}$, $G^{11}$, n, L, R, T, Q, W, X, Y, and Z and any other generic substituent symbol used herein.

Furthermore, when more than one assignment is given for any member or substituent, embodiments of this present disclosure comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this present disclosure for which $S_{example}$ is $S_1$; $S_{example}$ is $S_2$; $S_{example}$ is $S_3$; $S_{example}$ is one of Si and $S_2$; $S_{example}$ is one of Si and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^5$, $G^1$, $G^2$, $G^3$, $G^4$, $G^5$, $G^6$, $G^7$, $G^8$, $G^9$, $G^{10}$, $G^{11}$, n, L, R, T, Q, W, X, Y, and Z and any other generic substituent symbol used herein.

The nomenclature "$C_{i-j}$" with j>i, when applied herein to a class of substituents, is meant to refer to embodiments of this present disclosure for which each and every one of the number of carbon members, from i to j including i and j, is independently realized. By way of example, the term $C_{1-4}$ refers independently to embodiments that have one carbon member ($C_1$), embodiments that have two carbon members ($C_2$), embodiments that have three carbon members ($C_3$), and embodiments that have four carbon members ($C_4$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The present disclosure includes also pharmaceutically acceptable salts of the compounds of Formula (I), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmacopoeia or other generally recognized pharmacopoeia for use in animals, and more particularly, in humans.

A "pharmaceutically acceptable salt" is intended to mean a salt of a free acid or base of compounds represented by Formula (I) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.,* 2007, 50:6665-72, S. M. Berge, et al., "Pharmaceutical Salts", *J Pharm Sci.,* 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

The present disclosure also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

The present disclosure also relates to pharmaceutically active metabolites of the compounds of Formula (I), which may also be used in the methods of the present disclosure. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The term "stabilizer," as used herein, refers to polymers capable of chemically inhibiting or preventing degradation of a compound of Formula I. Stabilizers are added to formulations of compounds to improve chemical and physical stability of the compound.

The term "tablet," as used herein, denotes an orally administrable, single-dose, solid dosage form that can be produced by compressing a drug substance or a pharmaceutically acceptable salt thereof, with suitable excipients (e.g., fillers, disintegrants, lubricants, glidants, and/or surfactants) by conventional tableting processes. The tablet can be produced using conventional granulation methods, for example, wet or dry granulation, with optional comminution of the granules with subsequent compression and optional coating. The tablet can also be produced by spray-drying.

As used herein, the term "capsule" refers to a solid dosage form in which the drug is enclosed within either a hard or soft soluble container or "shell." The container or shell can be formed from gelatin, starch and/or other suitable substances.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

The term "combination," "therapeutic combination," "pharmaceutical combination," or "combination product" as used herein refer to a non-fixed combination or a kit of parts for the combined administration where two or more therapeutic agents can be administered independently, at the same time or separately within time intervals, especially where these time intervals allow that the combination partners show a cooperative, e.g., synergistic, effect.

The term "modulators" include both inhibitors and activators, where "inhibitors" refer to compounds that decrease, prevent, inactivate, desensitize, or down-regulate the activity and/or downstream signaling of an immune checkpoint inhibitor. For example, inhibition of an activity, e.g., PD-L1 activity, of at least 5%, 10%, 20%, 30%, 40% or more is included by this term. Thus, inhibition need not be 100%.

As used herein, the term "treatment" or "treating," is defined as the application or administration of a therapeutic agent, i.e., a compound of the present disclosure (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

In treatment methods according to the present disclosure, an effective amount of a pharmaceutical agent according to the present disclosure is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, for example about 0.05 to 100 mg/kg/day, or about 1 to 35 mg/kg/day, in single or divided dosage units (e.g., BID, TID, QID).

An example of a dose of a compound is from about 1 mg to about 2,500 mg. In some embodiments, a dose of a compound of the present disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

Compounds of the Disclosure

In one aspect, provided herein are compounds of Formula (I):

(I)

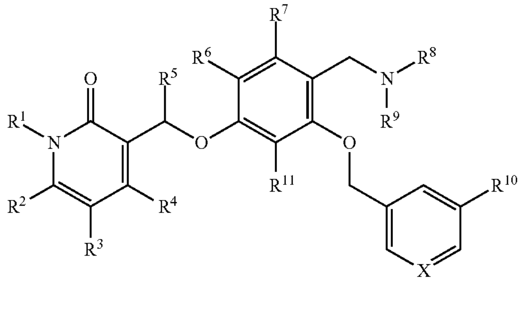

including the stereoisomers or tautomeric forms thereof, or a pharmaceutically acceptable salt thereof, wherein $R^1$ is a ring optionally substituted with one or more substituents selected from halogen, CN, $C_{1-6}$alkyl, $C_{1-6}$haloalkyl, $C_{3-6}$cycloalkyl, $C_{1-6}$heteroalkyl, $NR^xR^y$, $NR^xC(=O)R^y$, $NR^xCO_2R^y$, $NR^xC(=O)NR^xR^y$, $OC(=O)NR^xR^y$, O-(6 to 10-membered aryl), O-(5 to 10-membered heteroaryl), and a ring;

$R^2$, $R^3$, $R^4$, $R^5$, $R^6$, $R^7$ and $R^{11}$ are independently selected from H, halogen, $C_{1-4}$alkyl and $C_{1-4}$alkyl substituted with one or more F;

$R^8$ and $R^9$ are independently selected from H, $C_{1-6}$alkyl and $C_{1-6}$heteroalkyl, each of $C_{1-6}$alkyl and $C_{1-6}$heteroalkyl being optionally substituted with one or more substituents selected from $C_{1-4}$alkyl, OH, $OCH_3$, $—CO_2H$, $—CO_2C_{1-4}$alkyl, $C_{3-6}$heterocycle, aryl and heteroaryl;

wherein $C_{3-6}$heterocycle is optionally substituted with one or more substituents selected from oxo, OH and $CO_2H$;

with the proviso that $R^8$ and $R^9$ are not both H;

or wherein $R^8$ and $R^9$ are connected together to form a $C_{3-6}$heterocycle optionally substituted with one or more substituents selected from $C_{1-6}$alkyl, oxo, OH and $CO_2H$;

$R^{10}$ is selected from H, CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl)$_2$, $C(=O)NR^xR^y$, $SO_2$—$C_{1-6}$alkyl, aryl and heteroaryl;

wherein aryl and heteroaryl are optionally substituted with one or more substituents selected from CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$ alkyl-C(O)$NH_2$, $C_{1-6}$alkyl-CO—$NHC_{1-6}$alkyl, $C_{1-6}$alkyl-C(O)N($C_{1-6}$alkyl)$_2$, $C(=O)NR^xR^y$ and $SO_2$—$C_{1-6}$ alkyl;

X is N or $CR^{12}$;

$R^{12}$ is selected from H, F, Cl, CN, $C(=O)NR^xR^y$, aryl and heteroaryl, wherein aryl and heteroaryl are optionally substituted with one or more substituents selected from CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl)$_2$, $C(=O)NR^xR^y$ and $SO_2$—$C_{1-6}$alkyl; and $R^x$ and $R^y$ are independently selected from H and $C_{1-6}$alkyl.

In an embodiment, $R^1$ is a ring optionally substituted with one or more substituents selected from halogen, CN, $C_{1-6}$alkyl, $C_{1-6}$haloalkyl, $C_{3-6}$cycloalkyl, $C_{1-6}$heteroalkyl, $NR^xR^y$, $NR^xC(=O)R^y$, $NR^xCO_2R^y$, $NR^xC(=O)NR^xR^y$, $OC(=O)NR^xR^y$, and a ring.

In an embodiment, $R^1$ is 6 to 10-membered aryl, 5 to 10-membered heteroaryl, or 5 to 10-membered heterocycle optionally substituted with one or more substituents selected from halogen, CN, $C_{1-6}$alkyl, $C_{1-6}$haloalkyl, $C_{3-6}$cycloalkyl, $C_{1-6}$heteroalkyl, $NR^xR^y$, $NR^xC(=O)R^y$, $NR^xCO_2R^y$, $NR^xC(=O)NR^xR^y$, $OC(=O)NR^xR^y$, O-(6 to 10-membered aryl), O-(5 to 10-membered heteroaryl), 6 to 10-membered aryl, 5 to 10-membered heteroaryl, 5 to 10-membered heterocycle, and 5-10-membered cycloalkyl.

In an embodiment, $R^1$ is an optionally substituted monocyclic or bicyclic ring. In another embodiment, $R^1$ is an optionally substituted bicyclic ring. In yet another embodiment, $R^1$ is an optionally substituted bicyclic ring wherein the two rings of the bicycle are fused together or covalently bound to one another. In still another embodiment, $R^1$ is an optionally substituted bicyclic ring wherein the two rings of the bicycle are fused together.

In an embodiment, $R^1$ is an optionally substituted monocyclic or bicyclic aryl, heteroaryl, or heterocycle group. In another embodiment, $R^1$ is an optionally substituted bicyclic aryl, heteroaryl, or heterocycle group. In yet another embodiment, $R^1$ is an optionally substituted bicyclic aryl, heteroaryl, or heterocycle group wherein the two rings of the bicycle are fused together or covalently bound to one another. In still another embodiment, $R^1$ is an optionally substituted bicyclic aryl, heteroaryl, or heterocycle group wherein the two rings of the bicycle are fused together.

In an embodiment, $R^1$ is an optionally substituted ring wherein the ring optionally comprises one or more heteroatoms. In another embodiment, $R^1$ is an optionally substituted ring wherein the ring optionally comprises one or more heteroatoms each independently selected from O, S, and N. In yet another embodiment, $R^1$ is an optionally substituted ring wherein the ring optionally comprises one or more oxygen atoms.

In an embodiment, $R^1$ is an optionally substituted ring that is saturated. In another embodiment, $R^1$ is an optionally substituted ring that is unsaturated. In yet another embodiment, $R^1$ is an optionally substituted ring that is a combination of saturated and unsaturated.

In some embodiments, $R^1$ is selected from the following rings:

(g-1)

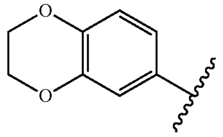

(g-2)

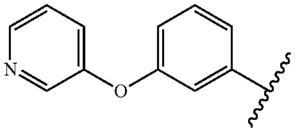

(g-3)

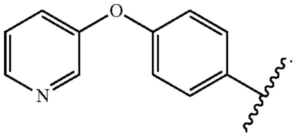

In some embodiments, $R^1$ is Formula (g-1):

(g-1)

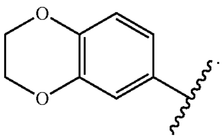

In some embodiments, $R^2$, $R^3$, $R^4$, $R^5$, $R^6$, $R^7$ and $R^{11}$ are independently selected from H and $C_{1-4}$alkyl.

In some embodiments, $R^2$, $R^3$, $R^4$, $R^5$, $R^7$ and $R^{11}$ are independently selected from H and $C_{1-4}$alkyl.

In some embodiments, $R^6$ is $C_{1-4}$alkyl or Cl.

In some embodiments, $R^6$ is Cl, and $R^2$, $R^3$, $R^4$, $R^5$, $R^7$ and $R^{11}$ are H.

In some embodiments, $R^a$ is H and $R^9$ is $C_{1-6}$alkyl substituted with OH and $CO_2H$.

In some embodiments, $R^8$ and $R^9$ are independently selected from H, $C_{1-6}$alkyl and $C_{1-6}$heteroalkyl, each of $C_{1-6}$alkyl and $C_{1-6}$heteroalkyl being optionally substituted with one, two, or three substituents selected from $C_{1-4}$alkyl, OH, $OCH_3$, —$CO_2H$, —$CO_2C_{1-4}$alkyl, aryl and heteroaryl.

In some embodiments, $R^8$ and $R^9$ are connected together to form a $C_{3-6}$heterocycle substituted with OH and $CO_2H$. In some embodiments, the $C_{3-6}$heterocycle is pyrrolidine.

In some embodiments, $R^{10}$ is selected from H and CN.

In some embodiments, $R^{12}$ is selected from H, Cl, and CN.

In some embodiments, $R^{10}$ is CN, and X is N.

In some embodiments, $R^{10}$ is H, and X is N.

Another embodiment of the present disclosure is a compound of formula (I) having an $IC_{50}$ equal or less than 5 μM. $IC_{50}$ can be measured using any means which are found appropriate by the person of average skill in the art, such as all or part of the means described cf. example 2 below.

A further embodiment of the present disclosure is a compound selected from the group consisting of the compounds described below, the stereoisomers or tautomeric forms thereof, or a pharmaceutically acceptable salt thereof:

compound 7

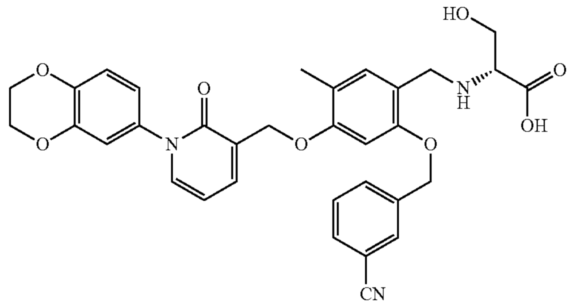

compound 8

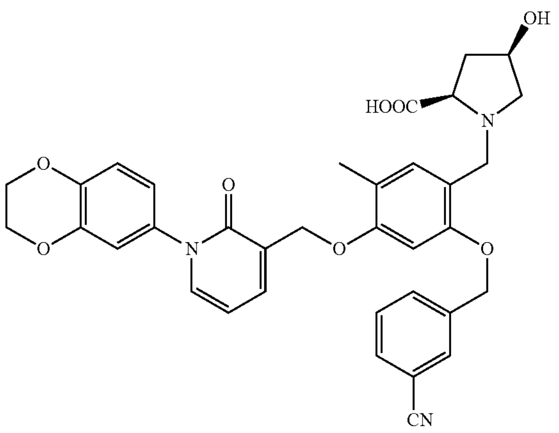

-continued compound 9

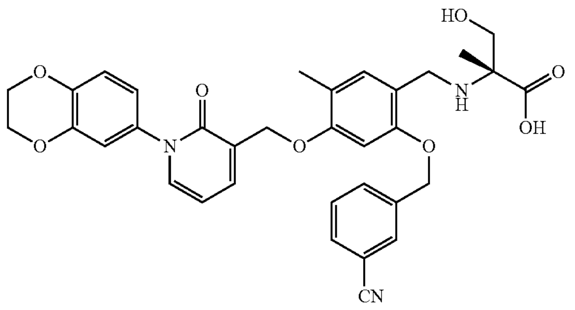

compound 10

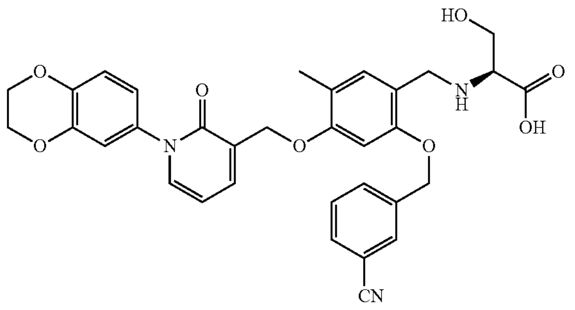

compound 11

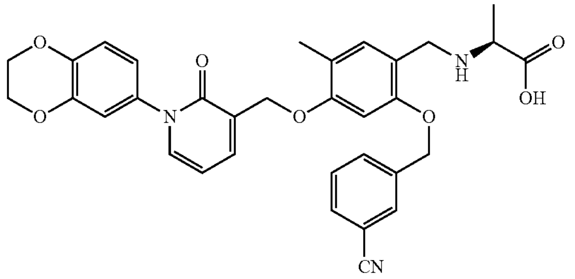

compound 12

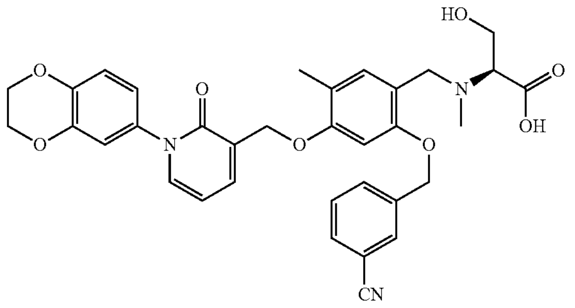

compound 101

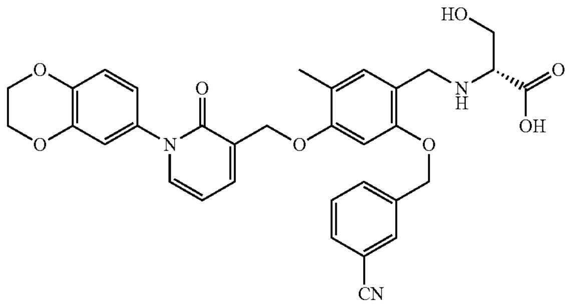

-continued compound 103

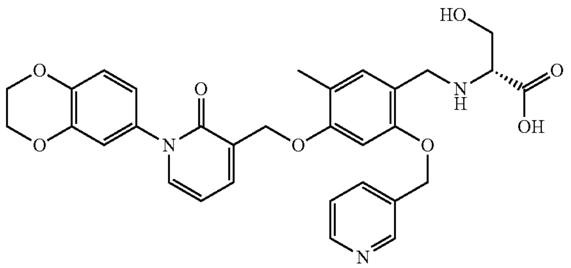

compound 202

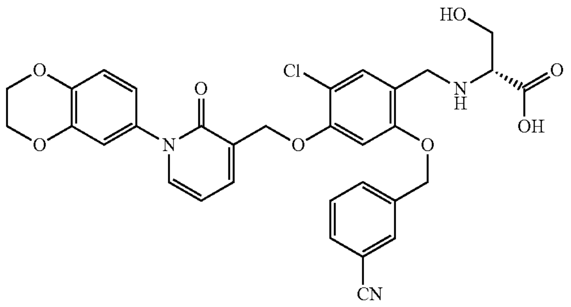

compound 203

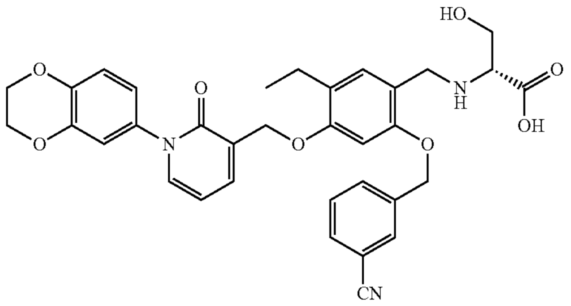

compound 204

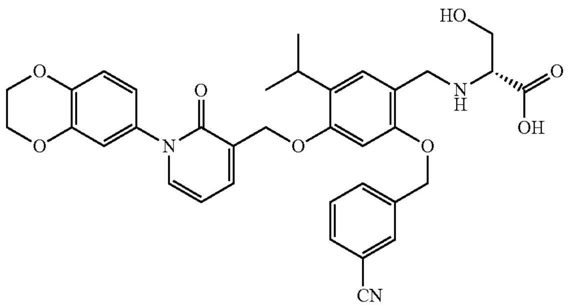

A further embodiment of the present disclosure is a compound selected from the group consisting of the compounds described below, the stereoisomers or tautomeric forms thereof, or a pharmaceutically acceptable salt thereof:

compound 205

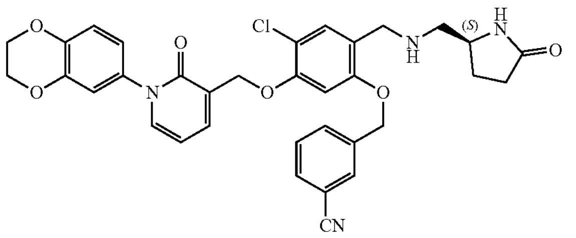

compound 207

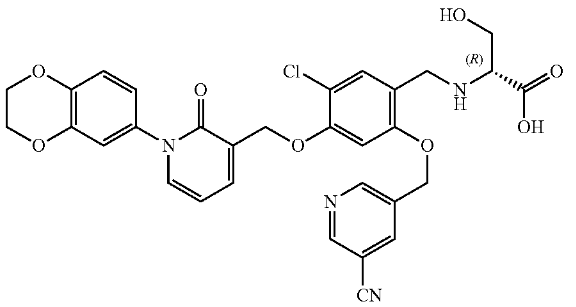

compound 209

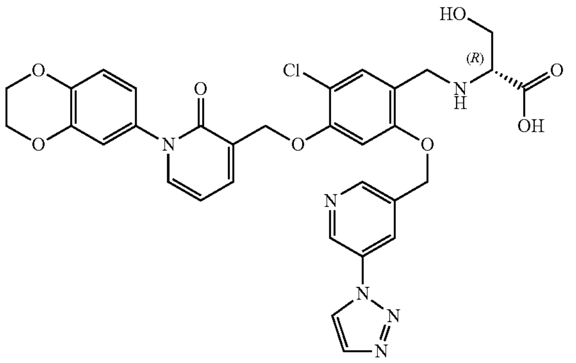

Pharmaceutical Compositions

In another aspect, provided herein are pharmaceutical compositions comprising (A) a compound of Formula (I):

(I)

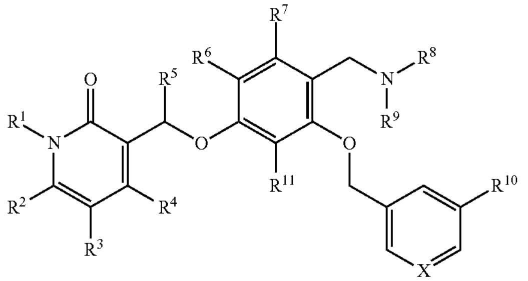

including the stereoisomers or tautomeric forms thereof, or a pharmaceutically acceptable salt thereof, wherein $R^1$ is a ring optionally substituted with one or more substituents selected from halogen, CN, $C_{1-6}$alkyl, $C_{1-6}$haloalkyl, $C_{3-6}$cycloalkyl, $C_{1-6}$heteroalkyl, $NR^xR^y$, $NR^xC(=O)R^y$, $NR^xCO_2R^y$, $NR^xC(=O)NR^xR^y$, $OC(=O)NR^xR^y$, O-(6 to 10-membered aryl), O-(5 to 10-membered heteroaryl), and a ring;

$R^2$, $R^3$, $R^4$, $R^5$, $R^6$, $R^7$ and $R^{11}$ are independently selected from H, halogen, $C_{1-4}$alkyl and $C_{1-4}$alkyl substituted with one or more F;

$R^8$ and $R^9$ are independently selected from H, $C_{1-6}$alkyl and $C_{1-6}$heteroalkyl, each of $C_{1-6}$alkyl and $C_{1-6}$heteroalkyl being optionally substituted with one or more substituents selected from $C_{1-4}$alkyl, OH, $OCH_3$, —$CO_2H$, —$CO_2C_{1-4}$alkyl, $C_{3-6}$heterocycle, aryl and heteroaryl;

wherein $C_{3-6}$heterocycle is optionally substituted with one or more substituents selected from oxo, OH and $CO_2H$;

with the proviso that $R^8$ and $R^9$ are not both H;

or wherein $R^8$ and $R^9$ are connected together to form a $C_{3-6}$heterocycle optionally substituted with one or more substituents selected from $C_{1-6}$alkyl, oxo, OH and $CO_2H$;

$R^{10}$ is selected from H, CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl)$_2$, C(═O)$NR^xR^y$, $SO_2$—$C_{1-6}$alkyl, aryl and heteroaryl;

wherein aryl and heteroaryl are optionally substituted with one or more substituents selected from CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl)$_2$, C(═O)$NR^xR^y$ and $SO_2$—$C_{1-6}$ alkyl;

X is N or $CR^{12}$;

$R^{12}$ is selected from H, F, Cl, CN, C(═O)$NR^xR^y$, aryl and heteroaryl;

wherein aryl and heteroaryl are optionally substituted with one or more substituents selected from CN, halogen, $C_{1-6}$alkyl, $OC_{1-6}$alkyl, $C_{1-6}$alkyl-$CO_2H$, $C_{1-6}$alkyl-$CO_2$—$C_{1-6}$alkyl, $C_{1-6}$alkyl-C(O)$NH_2$, $C_{1-6}$alkyl-CO—$NHC_{1-6}$alkyl, $C_{1-6}$alkyl-C(O)N($C_{1-6}$alkyl)$_2$, C(═O)$NR^xR^y$ and $SO_2$—$C_{1-6}$alkyl; and $R^x$ and $R^y$ are independently selected from H and $C_{1-6}$alkyl; and (B) at least one pharmaceutically acceptable carrier.

As used herein, the term "composition" or "pharmaceutical composition" refers to a mixture of at least one compound provided herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound provided herein within or to the patient such that it can perform its intended function. Typically, such constructs are carried or transported from one organ, or portion of the body, to another organ, or portion of the body. Each carrier must be "acceptable" in the sense of being compatible with the other ingredients of the formulation, including the compound provided herein, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound provided herein, and are physiologically acceptable to the patient. Supplementary active compounds can also be incorporated into the compositions. The "pharmaceutically acceptable carrier" can further include a pharmaceutically acceptable salt of the compound provided herein. Other additional ingredients that can be included in the pharmaceutical compositions provided herein are known in the art and described, for example in Remington's Pharmaceutical Sciences (Genaro, Ed., Mack Publishing Co., 1985, Easton, PA), which is incorporated herein by reference.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the present disclosure can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the present disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract or may be coated with an enteric coating.

Capsules for oral administration include hard and soft gelatin capsules. To prepare hard gelatin capsules, compounds of the present disclosure may be mixed with a solid, semi-solid, or liquid diluent. Soft gelatin capsules may be prepared by mixing the compound of the present disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this present disclosure may also be administered by non-oral routes. For example, the compositions may be formulated for rectal administration as a suppository. For parenteral use, including intravenous, intramuscular, intraperitoneal, or subcutaneous routes, the compounds of the present disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the present disclosure may utilize a patch formulation to affect transdermal delivery.

Compounds of the present disclosure may alternatively be administered in methods of this present disclosure by inhalation, via the nasal or oral routes, e.g., in a spray formulation also containing a suitable carrier.

Pharmaceutical Combinations and Kits

In another aspect, provided herein are pharmaceutical combinations comprising a first compound and a second compound as a combined preparation for simultaneous, separate or sequential use in the prevention or treatment of an infection or cancer in a subject in need thereof, wherein the first compound is different from the second compound. In an embodiment, the first compound is a compound of Formula (I), including the stereoisomers or tautomeric forms thereof, or a pharmaceutically acceptable salt thereof. In another embodiment, the first compound is a pharmaceutical composition comprising (A) a compound of Formula (I), including the stereoisomers or tautomeric forms thereof, or a pharmaceutically acceptable salt thereof, and (B) at least one pharmaceutically acceptable carrier. In yet another embodiment, the second compound is an ingredient active against said infection or cancer.

In an embodiment, the pharmaceutical combination is for use in the prevention or treatment of an infection. In another embodiment, the infection is a bacterial, viral, or fungal infection. In yet another embodiment, the infection is a viral infection. In still another embodiment, the infection is a chronic or latent viral infection. In another embodiment, the infection is a chronic viral infection.

By nonlimiting example, infections caused by the following viruses may be treated or prevented by the pharmaceutical combinations of the disclosure: hepatitis viruses (more particularly, hepatitis A, hepatitis B (HBV), hepatitis C, and hepatitis D), human immunodeficiency virus (HIV), herpes virus, papillomaviruses, and influenza. Preferably, the viral infection to be treated or prevented is HBV, HIV, or HBV and HIV.

HBV infections that may be treated according to the disclosed methods include HBV genotype A, B, C, and/or D infections. However, in an embodiment, the methods disclosed may treat any HBV genotype ("pan-genotypic treatment"). HBV genotyping may be performed using methods known in the art, for example, INNO-LIPA® HBV Genotyping, Innogenetics N.V., Ghent, Belgium).

In an embodiment, the second compound is an HBV inhibitor or an HIV inhibitor. In another embodiment, the second compound is an HBV inhibitor. In an exemplary embodiment, the second compound is an active ingredient that is known or discovered to be effective in the treatment of conditions or disorders involved in HBV infection, such as another PD-L1 inhibitor or a compound active against another target associated with the particular condition or disorder involved in HBV infection, or the HBV infection itself. The combination may serve to increase efficacy (e.g., by including in the combination a compound potentiating the potency or effectiveness of an active agent according to the present disclosure), decrease one or more side effects, or decrease the required dose of the active agent according to the present disclosure. In a further embodiment, the methods provided herein allow for administering of the at least one additional therapeutic agent at a lower dose or frequency as compared to the administering of the at least one additional therapeutic agent alone that is required to achieve similar results in prophylactically treating an HBV infection in an individual in need thereof.

Such compounds include but are not limited to HBV combination drugs, HBV vaccines, HBV DNA polymerase inhibitors, immunomodulators, toll-like receptor (TLR) modulators, interferon alpha receptor ligands, hyaluronidase inhibitors, hepatitis B surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucleotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 simulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and any other agent that affects the HBV life cycle and/or affects the consequences of HBV infection or combinations thereof.

In an embodiment, the pharmaceutical combination is for use in the prevention or treatment of cancer. By nonlimiting example, cancers that may be prevented or treated by the disclosed methods include melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and hematological malignancies.

In an embodiment, the second compound is an anti-cancer agent selected from the group consisting of chemotherapeutic agents, cytotoxic agents, radio-therapeutic agents, antineoplastic agents, and anti-proliferative agents.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve, and combination index curve, respectively.

Uses of the Compounds of the Disclosure

The present disclosure also provides therapeutic and prophylactic methods, which include administering to a subject having a PD-L1-associated disease (e.g., an infectious disease or cancer), a compound of Formula (I), including the stereoisomers or tautomeric forms thereof, or a pharmaceutically acceptable salt thereof, or a pharmaceutical composition comprising (A) a compound of Formula (I), including the stereoisomers or tautomeric forms thereof, or a pharmaceutically acceptable salt thereof, and (B) at least one pharmaceutically acceptable carrier.

In an aspect, the disclosure relates to a compound or a pharmaceutical composition of the disclosure for use as a medicament.

In another aspect, the disclosure relates to a compound or a pharmaceutical composition of the disclosure for use in the prevention or treatment of an infectious disease in a subject in need thereof. Infectious diseases that can be prevented and/or treated by the compounds and pharmaceutical compositions of the disclosure are caused by infectious agents, including but not limited to bacteria, fungi, or viruses. Thus, in embodiments of this aspect of the disclosure, the compound or pharmaceutical composition is useful in the prevention or treatment of a bacterial, viral, or fungal infectious disease. Preferably, the compound or pharmaceutical composition is useful in the treatment of a viral infectious disease.

By nonlimiting example, viral diseases or infections that may be treated by the compounds and pharmaceutical compositions of the disclosure include hepatitis virus (e.g., hepatitis A, hepatitis B (HBV), hepatitis C, hepatitis D), influenza, varicella, adenovirus, herpes virus (e.g., herpes simplex type I (HSV-1), herpes simplex type II (HSV-II)), rinderpest, rhinovirus, echovirus, rotavirus, respiratory syncytial virus, papillomavirus, papova virus, cytomegalovirus, echinovirus, arbovirus, huntvirus, coxsackie virus, mumps virus, measles virus, rubella virus, polio virus, small pox, Epstein Barr virus, human immunodeficiency virus (HIV), and agents of viral diseases such as viral meningitis, encephalitis, dengue, or small pox.

Exemplary viral diseases or infections that may be treated by the compounds and pharmaceutical compositions of the disclosure include hepatitis virus (e.g., hepatitis A, hepatitis B (HBV), hepatitis C, hepatitis D), influenza, herpes virus (e.g., herpes simplex type I (HSV-1), herpes simplex type II (HSV-II)), papillomavirus, or human immunodeficiency virus (HIV). In a preferred embodiment, the viral disease or infection to be treated is HBV or HIV.

In another aspect, the disclosure relates to a compound or a pharmaceutical composition of the disclosure for use in the prevention or treatment of an HIV infection, an HBV infection, an HIV-induced disease, or an HBV-induced disease in a subject in need thereof. In a preferred embodiment, the disclosure relates to a compound or a pharmaceutical composition of the disclosure for use in the prevention or treatment of an HBV infection or an HBV-induced disease in a subject in need thereof.

The disclosure also provides methods of treating, preventing, and reducing the severity of chronic viral infections in a subject. In an aspect, the disclosure relates to a compound or a pharmaceutical composition of the disclosure for use in the prevention or treatment of a chronic viral infection. Nonlimiting exemplary chronic viral infections include HIV and chronic hepatitis B. In a preferred embodiment, the disclosure relates to a compound or a pharmaceutical composition of the disclosure for use in the prevention or treatment of chronic hepatitis B in a subject in need thereof.

In an embodiment, the disclosure relates to a method of treating a chronic viral infection, more particularly a HBV and/or HIV infection, in a subject in need thereof, comprising administering to the subject a therapeutically effective amount of a compound or a pharmaceutical composition of the disclosure.

In another embodiment, the disclosure relates to a method of reducing the viral load associated with a chronic viral infection, more particularly a HBV and/or HIV infection, in a subject in need thereof, comprising administering to the subject a therapeutically effective amount of a compound or a pharmaceutical composition of the disclosure.

In yet another embodiment, the disclosure relates to a method of reducing reoccurrence of a chronic viral infection, more particularly of a HBV and/or HIV infection, in a subject in need thereof, comprising administering to the subject a therapeutically effective amount of a compound or a pharmaceutical composition of the disclosure.

In still another embodiment, the disclosure relates to a method of reducing an adverse physiological impact of a chronic viral infection, more particularly of a HBV and/or HIV infection, in a subject in need thereof, comprising administering to the subject a therapeutically effective amount of a compound or a pharmaceutical composition of the disclosure.

In an embodiment, the disclosure relates to a method of inducing remission of hepatic injury from an HBV infection in a subject in need thereof, comprising administering to the subject a therapeutically effective amount of a compound or a pharmaceutical composition of the disclosure.

In an embodiment, the disclosure relates to a method of treating a latent viral infection, more particularly a latent HBV and/or HIV infection, in a subject in need thereof, comprising administering to the subject a therapeutically effective amount of a compound or a pharmaceutical composition of the disclosure.

In an embodiment of the uses and methods above, treatment or prevention of the viral infection may further comprise administering to the subject at least one additional therapeutic agent. Exemplary additional therapeutic agents include HBV polymerase inhibitors, nucleic acid analogs, interferons, viral entry inhibitors, viral maturation inhibitors, capsid assembly modulators, reverse transcriptase inhibitors, TLR agonists, small interfering RNAs, antisense oligonucleotides, nucleic acid polymers, and combinations thereof.

In an embodiment of the uses and methods above, the subject has an HIV infection or a chronic HBV infection. In some embodiments, the subject is a chronically HBV-infected subject, with or without evidence of underlying liver inflammation.

Efficacy of treatment of an infectious disease can be demonstrated, for example, by a decrease in the presence of the infectious agent as demonstrated by an inability to culture the agent from a subject sample. Efficacy of treatment of an infectious disease can be demonstrated by a decrease in the presence of the infectious agent as demonstrated, for example, by a decrease in a protein, nucleic acid, or carbohydrate present in the infectious agent. Efficacy of treatment can be demonstrated, for example, by the presence of an immune response as demonstrated by the presence of antibodies or immune cells targeted against the infectious agent. Efficacy of treatment of an infectious disease can be demonstrated by a decrease in the presence of the infectious agent as demonstrated, for example, by a decrease in one or more signs or symptoms of the infection, e.g., fever, pain, nausea, vomiting, abnormal blood chemistry, weight loss. The specific signs or symptoms will depend on the specific pathogen. Efficacy of treatment of an infectious disease can be demonstrated by the development of antibodies or immune cells targeting the pathogen.

In another aspect, the disclosure relates to a compound or a pharmaceutical composition of the disclosure for use in the treatment of cancer in a subject in need thereof. In particular, the compound or pharmaceutical composition may be useful in the inhibition of growth, proliferation, or metastasis of cancer cells in the subject. Cancer refers to any of various malignant neoplasms characterized by the proliferation of anaplastic cells that tend to invade surrounding tissue and metastasize to new body sites and also refers to the pathological condition characterized by such malignant neoplastic growths. By nonlimiting example, the cancer may be prostate cancer, lung cancer, breast cancer, colorectal cancer, bladder cancer, pancreatic cancer, endometrial cancer, ovarian cancer, bone cancer, esophageal cancer, liver cancer, stomach cancer, brain tumors, cutaneous melanoma, and/or leukemia.

In an embodiment, the cancer can be a solid tumor. In another embodiment, the cancer can be a hematological cancer. In yet another embodiment, the cancer is a solid tumor selected from the group consisting of squamous cell carcinoma, non-squamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST).

In an embodiment, the cancer is a solid tumor selected from non-small cell lung cancer (NSCLC), hepatocellular carcinoma, melanoma, ovarian cancer, breast cancer, pancreatic cancer, renal cell carcinoma, colorectal cancer, or prostate cancer. In another embodiment, the cancer can be non-small cell lung cancer (NSCLC). In yet another embodiment, the cancer can be hepatocellular carcinoma. In still another embodiment, the cancer can be melanoma. In an embodiment, the cancer can be ovarian cancer. In another embodiment, the cancer can be breast cancer. In yet another embodiment, the cancer can be pancreatic cancer. In still another embodiment, the cancer can be renal cell carcinoma. In an embodiment, the cancer can be colorectal cancer. In another embodiment, the cancer can be prostate cancer.

In an embodiment, the cancer is selected from melanoma; metastatic non-small cell lung cancer; squamous non-small cell lung cancer; non-squamous non-small cell lung cancer; squamous cell carcinoma of the head and neck; renal cell carcinoma; Hodgkin's lymphoma; cutaneous squamous cell carcinoma; hepatocellular carcinoma; pancreatic carcinoma; urothelial carcinoma; metastatic merkel-cell carcinoma; colorectal cancer; castration-resistant prostate cancer; ovarian cancer; gastric cancer; carcinomas of the esophagus, gastrointestinal tract, and breast; and hematological malignancies.

In an embodiment of the uses and methods above, treatment or prevention of the cancer may further comprise administering to the subject at least one additional therapeutic agent. Exemplary additional therapeutic agents include chemotherapeutic agents, cytotoxic agents, radiotherapeutic agents, anti-neoplastic agents, anti-proliferative agents, and combinations thereof.

Efficacy of treatment of cancer can be demonstrated by stabilization or a decrease in tumor burden as demonstrated by a stabilization or decrease in tumor burden of the primary tumor, metastatic tumors, or the delay or prevention of tumor metastasis.

In another aspect, the disclosure relates to a compound or a pharmaceutical composition of the disclosure for use in a method for enhancing, stimulating, modulating, or increasing the immune response in a subject in need thereof. Under certain circumstances, it may be desirable to elicit or enhance a patient's immune response in order to treat an immune disorder or cancer. Immune disorders that may be treated or prevented by the disclosed methods include but are not limited to bacterial infections, fungal infections, viral infections, and cancer. In an embodiment, the enhancement, stimulation, modulation, or increase in the immune response may be a result of T cell activation by a compound or pharmaceutical composition of the disclosure. In another embodiment, the compound or pharmaceutical composition may be used to inhibit or reduce the downregulatory activity associated with PD-L1 (i.e., downregulation of T cell proliferation and activation).

In another aspect, the disclosure relates to a compound or a pharmaceutical composition of the disclosure for use as an immune checkpoint inhibitor. In particular, the compound or pharmaceutical composition is useful as a PD-L1 checkpoint inhibitor. Efficacy of the compounds of the disclosure as PD-L1 inhibitors may be demonstrated, for example, by the biological assays disclosed herein.

Preparation Methods

An aspect of the disclosure relates to a process for the preparation of a compound of Formula (I) as described herein.

In an embodiment, the process comprises at least the step of reacting a compound of Formula (II), (II)

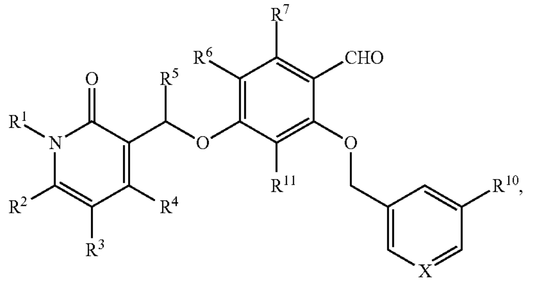

with an amine of Formula (III), (III)

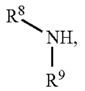

in the presence of sodium cyanoborohydride, wherein $R^1$, $R^2$, $R^3$, $R^4$, $R^5$, $R^6$, $R^7$, $R^8$, $R^9$, $R^{10}$, $R^{11}$ and X have been defined herein.

EXAMPLES

The following examples are merely illustrative and are not intended to limit the disclosure to the materials, conditions, or process parameters set forth therein.

Example 1: Preparation of Compounds of the Disclosure

Scheme 1. Synthesis of Compound 7

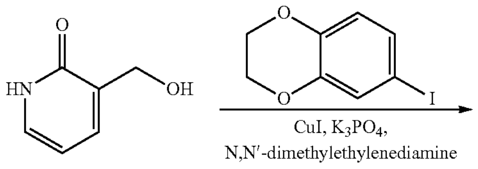

1

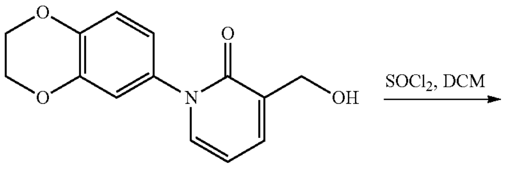

2

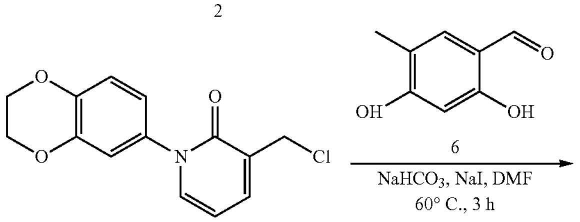

3

-continued

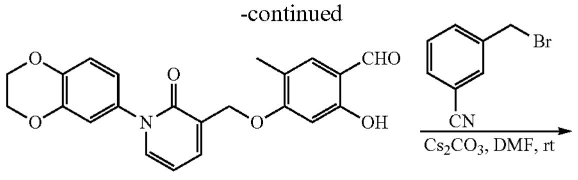

4

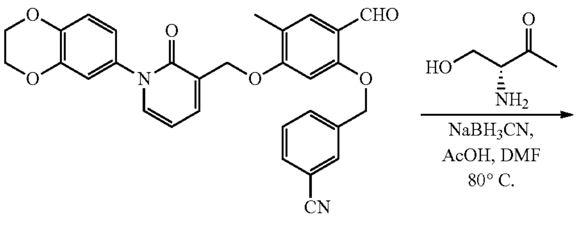

5

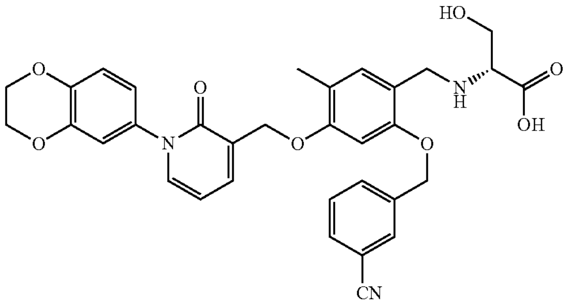

7

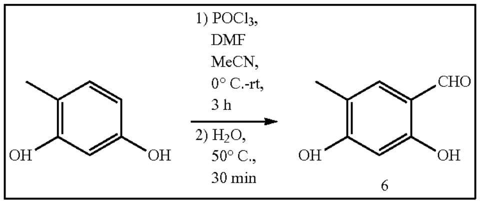

6

Synthesis of 1-(2,3-dihydrobenzo[b][1,4]dioxin-6-yl)-3-(hydroxymethyl)pyridin-2(1H)-one

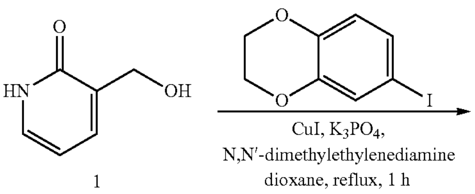

1

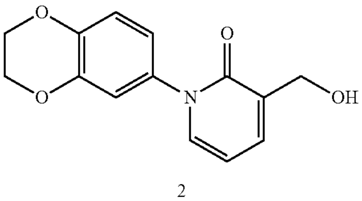

2

To a solution of 3-(hydroxymethyl)pyridin-2(1H)-one (5 g, 39.960 mmol) in 1,4-dioxane (50 mL) was added 6-iodo-2,3-dihydrobenzo[b][1,4]dioxine (12.566 g, 47.952 mmol), CuI (765 mg, 3.996 mmol), $K_3PO_4$ (16.964 g, 79.920 mmol) and N,N'-dimethylethylenediamine (929 mg, 7.992 mmol)

under $N_2$ atmosphere. The resulting mixture was maintained under nitrogen and stirred at 110° C. for overnight. After cooling down to rt, the reaction was quenched with water (100 mL). The resulting mixture was extracted with ethyl acetate (3×100 mL). The organic layers were combined, dried over anhydrous sodium sulfate, the solids were removed by filtration and the filtrate was concentrated under reduced pressure. The crude was purified by silica gel chromatography (0 to 15% $CH_3OH/CH_2Cl_2$) to afford the titled compound as a white solid (4.4 g, 42%). LC/MS: mass calcd. for $C_{14}H_{13}NO_4$: 259.08, found: 260.15 [M+H]+.

Synthesis of 3-(chloromethyl)-1-(2,3-dihydrobenzo[b][1,4]dioxin-6-yl)pyridin-2(1H)-one

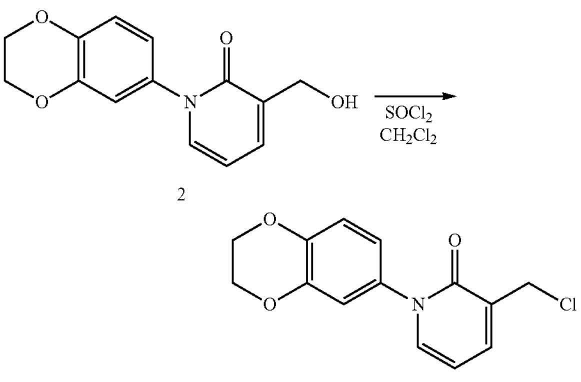

2

3

To a solution of 1-(2,3-dihydrobenzo[b][1,4]dioxin-6-yl)-3-(hydroxymethyl)pyridin-2(1H)-one (2 g, 7.714 mmol) in $CH_2Cl_2$ (20 mL) was added $SOCl_2$ (1.836 g, 15.429 mmol). The resulting mixture was stirred at rt for overnight. The mixture was concentrated under reduced pressure, and the crude was purified by silica gel chromatography (0 to 15% $CH_3OH/CH_2Cl_2$) to afford the titled compound as a white solid (2 g, 93%). LC/MS: mass calcd. for $C_{14}H_{12}ClNO_3$: 277.05, found: 278.00 [M+H]+.

Synthesis of 2,4-dihydroxy-5-methylbenzaldehyde

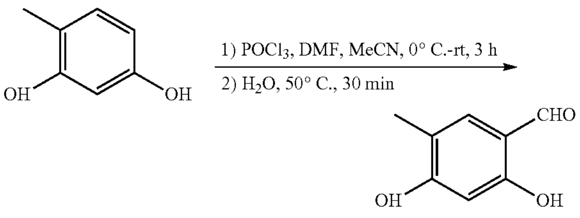

6

To a solution of 4-methylbenzene-1,3-diol (5.0 g, 40.278 mmol) and DMF (4.6 mL, 2.0 eq.) in $CH_3CN$ (70 ml) was added phosphoryl trichloride (6.3 mL, 1.2 eq.) at 0° C. The reaction was stirred at room temperature for 3 hours and the solid was isolated by filtration. The yellow solid was washed with cooled $CH_3CN$ (10 mL), and $H_2O$ (30 mL) was added. The resulting mixture was stirred at 50° C. for 30 min and cooled to room temperature, filtered to afford 2,4-dihydroxy-5-methylbenzaldehyde as white solid (4 g, 64%). LC/MS: mass calcd. for $C_8H_8O_3$: 152.05, found: 153.10 [M+H]+.

Synthesis of 4-((1-(2,3-dihydrobenzo[b][1,4]dioxin-6-yl)-2-oxo-1,2-dihydropyridin-3-yl)methoxy)-2-hydroxy-5-methylbenzaldehyde

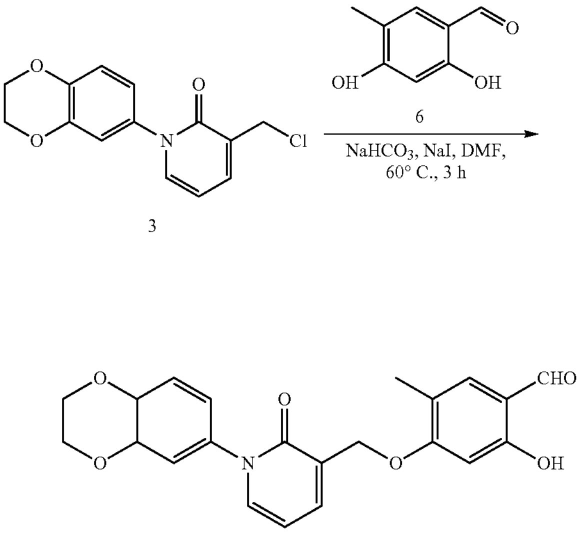

6

3

4

To a solution of 3-(chloromethyl)-1-(2,3-dihydrobenzo[b][1,4]dioxin-6-yl)pyridin-2(1H)-one (4 g, 14.404 mmol) in DMF (40 mL) was added 2,4-dihydroxy-5-methylbenzaldehyde (2.411 g, 15.844 mmol), $NaHCO_3$ (1.815 g, 21.606 mmol), NaI (1.08 g, 7.202 mmol). The mixture was stirred at 60° C. for 4 h. After cooling to rt, the reaction was quenched with water (100 mL), and extracted with ethyl acetate (3×100 mL). The organic layers were combined, dried over anhydrous sodium sulfate, the solids were removed by filtration and the solvent of the filtrate was removed under reduced pressure. The crude was purified by silica gel chromatography (0 to 15% $CH_3OH/CH_2Cl_2$) to afford the titled compound as a white solid (3.5 g, 62%). LC/MS: mass calcd. for $C_{22}H_{19}NO_6$: 393.12, found: 394.10 [M+H]+.

Synthesis of 3-((5-((1-(2,3-dihydrobenzo[b][1,4]dioxin-6-yl)-2-oxo-1,2-dihydropyridin-3-yl)methoxy)-2-formyl-4-methylphenoxy)methyl)benzonitrile

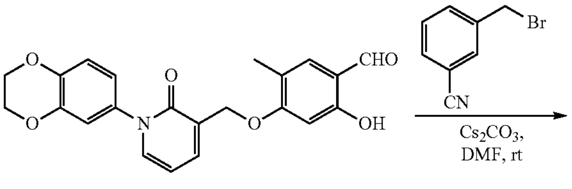

4

-continued

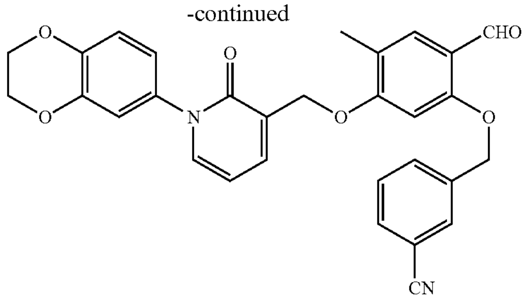

5

To a solution of 4-((1-(2,3-dihydrobenzo[b][1,4]dioxin-6-yl)-2-oxo-1,2-dihydropyridin-3-yl)methoxy)-2-hydroxy-5-methylbenzaldehyde (3.5 g, 8.897 mmol) in DMF (35 mL) was added 3-(bromomethyl)benzonitrile (2.093 g, 10.68 mmol), $Cs_2CO_3$ (4.348 g, 13.346 mmol). The resulting mixture was stirred at rt for overnight. Then the reaction was quenched with water (50 mL). The resulting mixture was extracted with ethyl acetate (3×50 mL). The organic layers were combined, dried over anhydrous sodium sulfate, filtered and concentrated. The crude was purified by silica gel chromatography (0 to 15% $CH_3OH/CH_2Cl_2$) to afford the titled compound as a white solid (3.0 g, 66%). LC/MS: mass calcd. for $C_{30}H_{24}N_2O_6$: 508.16, found: 509.10 [M+H]+.

Synthesis of (2-((3-cyanobenzyl)oxy)-4-((1-(2,3-dihydrobenzo[b][1,4]dioxin-6-yl)-2-oxo-1,2-dihydropyridin-3-yl)methoxy)-5-methylbenzyl)-D-serine

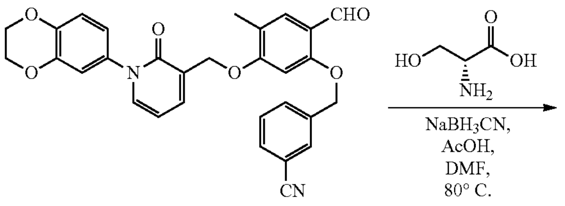

5

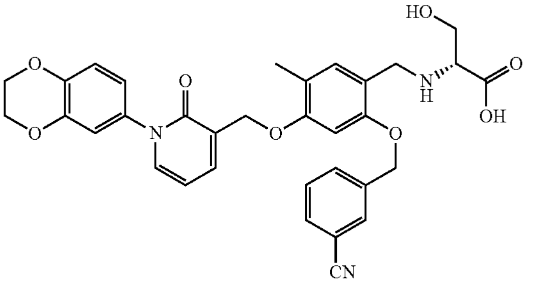

7

To a mixture of 3-((5-((1-(2,3-dihydrobenzo[b][1,4]dioxin-6-yl)-2-oxo-1,2-dihydropyridin-3-yl)methoxy)-2-formyl-4-methylphenoxy)methyl)benzonitrile (508 mg, 1 mmol), D-serine (105 mg, 0.999 mmol) and sodium cyanoborohydride (63 mg, 1.003 mmol) was added acetic acid (5 mL) and DMF (15 mL) respectively. And the mixture was maintained under nitrogen and stirred at 80° C. for 3 h. The reaction cooled to rt, and the solvent was removed under reduced pressure. The crude was purified by silica gel chromatography (0 to 20% ethyl acetate/petroleum ether) to afford 400 mg crude product, purified by preparatory HPLC with the following conditions: XBridge Prep OBD C18, 30×150 mm, 5 um; mobile phase A: Water (10 mmol/L $NH_4HCO_3$), mobile phase B: ACN; flow rate: 60 mL/min; Gradient: 40% B to 75% B in 9 min; 220 nm; Rt: 8.99 min. After lyophilization, the titled compound was obtained as white solid (340 mg, 56%). LC/MS: mass calcd. for 597.21, found $C_{33}H_{31}N_3O_8$: 598.20 [M+H]+. $^1H$ NMR (400 MHz, DMSO-$d_6$) δ 7.99 (d, J=1.8 Hz, 1H), 7.89 (dt, J=8.0, 1.4 Hz, 1H), 7.81 (dt, J=7.8, 1.4 Hz, 1H), 7.65-7.55 (m, 3H), 7.19 (s, 1H), 7.01-6.94 (m, 2H), 6.91-6.84 (m, 2H), 6.35 (t, J=6.8 Hz, 1H), 5.29-5.17 (m, 2H), 4.98 (s, 2H), 4.30 (s, 4H), 3.95-4.08 (m, 2H), 3.75 (dd, J=11.3, 4.5 Hz, 1H), 3.64 (dd, J=11.3, 6.8 Hz, 1H), 3.19-3.13 (m, 1H), 2.15 (s, 3H).

Synthesis of (2R,4R)-1-(2-((3-cyanobenzyl)oxy)-4-((1-(2,3-dihydrobenzo[b][1,4]dioxin-6-yl)-2-oxo-1,2-dihydropyridin-3-yl)methoxy)-5-methylbenzyl)-4-hydroxypyrrolidine-2-carboxylic acid

8

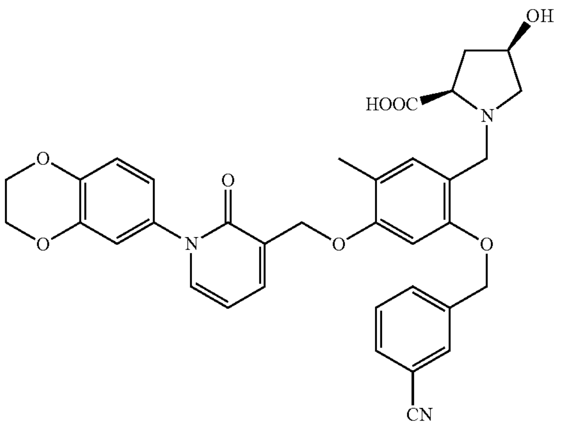

The titled compound was prepared according to the method to prepare 7. The crude was purified by silica gel chromatography (0 to 20% ethyl acetate/petroleum ether) then by preparatory HPLC with the following conditions: Column: XBridge Prep OBD C18 Column, 30×150 mm, 5□m; Mobile Phase A: Water (10 mmol/L $NH_4HCO_3$), Mobile Phase B: ACN; Flow rate: 60 mL/min; Gradient: 40% B to 75% B in 9 min; 220 nm; Rt: 8.99 min. After lyophilization, the titled compound was obtained as white solid (232.3 mg, 37%). LC/MS: mass calcd. for 623.23, found $C_{35}H_{33}N_3O_8$: 624.3 [M+H]+. $^1H$ NMR (400 MHz, DMSO-$d_6$) δ 7.95 (d, J=2.0 Hz, 1H), 7.91-7.84 (m, 1H), 7.81 (dt, J=7.8, 1.4 Hz, 1H), 7.66-7.55 (m, 3H), 7.16 (s, 1H), 6.98 (dd, J=5.5, 3.0 Hz, 2H), 6.91-6.84 (m, 2H), 6.35 (t, J=6.8 Hz, 1H), 5.30-5.18 (m, 2H), 4.97 (s, 2H), 4.30 (s, 4H), 4.20 (s, 1H), 4.06 (d, J=13.0 Hz, 1H), 3.91 (d, J=12.9 Hz, 1H), 3.48 (dd, J=10.0, 4.5 Hz, 1H), 2.99 (d, J=10.9 Hz, 1H), 2.84 (dd, J=10.9, 4.6 Hz, 1H), 2.34-2.26 (m, 1H), 2.14 (s, 3H), 1.90 (d, J=13.2 Hz, 1H).

Synthesis of (R)-2-((2-((3-cyanobenzyl)oxy)-4-((1-(2,3-dihydrobenzo[b][1,4]dioxin-6-yl)-2-oxo-1,2-dihydropyridin-3-yl)methoxy)-5-methylbenzyl)amino)-3-hydroxy-2-methylpropanoic acid

9

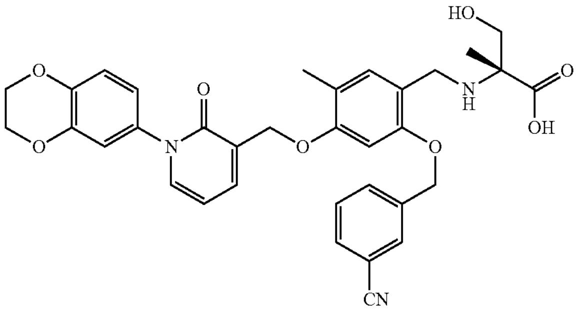

The titled compound was made according to the procedure to make compound 7, and was purified by reverse phase C18 column (0-60% $H_2O$ (0.5% TFA)/ACN) to afford the titled compound as a white solid (140 mg, 29%). LC/MS: mass calcd. for $C_{34}H_{33}N_3O_8$: 611.23, found: 612.3 [M+H]+. $^1H$ NMR (300 MHz, DMSO-$d_6$) δ 7.96 (s, 1H), 7.89 (d, J=8.2 Hz, 1H), 7.79 (d, J=7.7 Hz, 1H), 7.65-7.52 (m, 3H), 7.24 (s, 1H), 7.01-6.92 (m, 2H), 6.91-6.78 (m, 2H), 6.34 (t, J=6.8 Hz, 1H), 5.22 (s, 2H), 4.98 (s, 2H), 4.29 (s, 4H), 4.01 (s, 2H), 3.67 (d, J=11.4 Hz, 2H), 3.63-3.48 (m, 2H), 2.15 (s, 3H), 1.28 (s, 3H).

Synthesis of (2-((3-cyanobenzyl)oxy)-4-((1-(2,3-dihydrobenzo[b][1,4]dioxin-6-yl)-2-oxo-1,2-dihydropyridin-3-yl)methoxy)-5-methylbenzyl)-L-serine

10

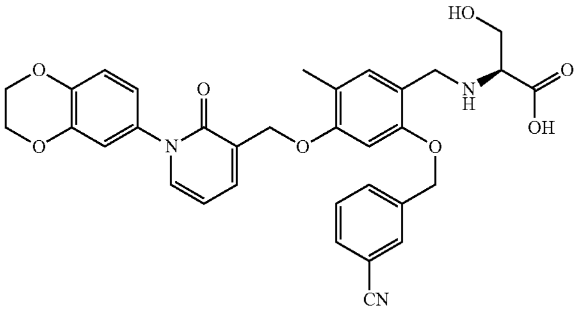

The titled compound was made according to the procedure to make compound 7, and was purified by reverse phase C18 column (0 to 60% $H_2O$ (0.5% TFA)/ACN) to afford the titled compound as a white solid (140 mg, 29%). LC/MS: mass calcd. for 597.21, found $C_{33}H_{31}N_3O_8$: 598.2 [M+H]+. $^1H$ NMR (400 MHz, DMSO-$d_6$) δ 7.99 (d, J=1.8 Hz, 1H), 7.89 (dt, J=8.0, 1.4 Hz, 1H), 7.81 (dt, J=7.8, 1.4 Hz, 1H), 7.65-7.55 (m, 3H), 7.19 (s, 1H), 7.01-6.94 (m, 2H), 6.91-6.84 (m, 2H), 6.35 (t, J=6.8 Hz, 1H), 5.29-5.17 (m, 2H), 4.98 (s, 2H), 4.30 (s, 4H), 3.95-4.08 (m, 2H), 3.75 (dd, J=11.3, 4.5 Hz, 1H), 3.64 (dd, J=11.3, 6.8 Hz, 1H), 3.19-3.13 (m, 1H), 2.15 (s, 3H).

Synthesis of 2-((3-chlorobenzyl)oxy)-4-((1-(2,3-dihydrobenzo[b][1,4]dioxin-6-yl)-2-oxo-1,2-dihydropyridin-3-yl)methoxy)-5-methylbenzaldehyde

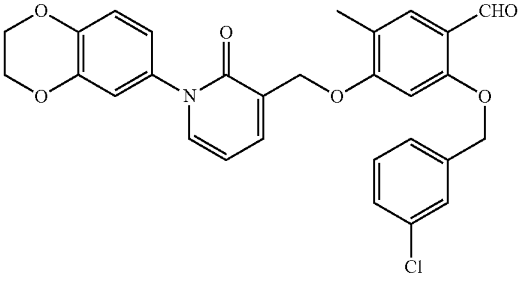

100

Compound 100 was made using a procedure analogous to the procedure to prepare compound 5.

Synthesis of (2-((3-chlorobenzyl)oxy)-4-((1-(2,3-dihydrobenzo[b][1,4]dioxin-6-yl)-2-oxo-1,2-dihydropyridin-3-yl)methoxy)-5-methylbenzyl)-D-serine

100

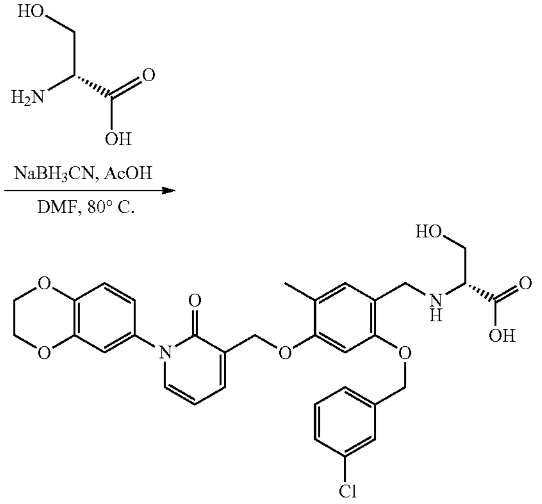

101

To a mixture of 3-((5-((1-(2,3-dihydrobenzo[b][1,4]dioxin-6-yl)-2-oxo-1,2-dihydropyridin-3-yl)methoxy)-2-formyl-4-methylphenoxy)methyl)benzonitrile (480 mg, 0.927 mmol) and D-serine (389.5 mg, 3.707 mmol) in DMF (5 mL) was added acetic acid (5.5 mg, 0.093 mmol) and the mixture was stirred at rt for 30 min. Then $NaCNBH_3$ (204 mg, 3.244 mmol) was added and the mixture was heated at 80° C. for 3 h. The reaction was then cooled to rt. The mixture was dropwise added in water at 0° C., The crude obtained was purified by reverse phase C18 column (0 to 60% $H_2O$ (0.5% TFA)/ACN) to afford the titled compound as a white solid (46.7 mg, 8%). LC/MS: mass calcd. for $C_{32}H_{31}ClN_2O_8$: 607.18, found: 607.2[M+H]+. $^1H$ NMR (300 MHz, DMSO-$d_6$) δ 7.64-7.55 (m, 3H), 7.52-7.43 (m, 1H), 7.43-7.30 (m, 2H), 7.24 (s, 1H), 7.02-6.92 (m, 2H), 6.91-6.81 (m, 2H), 6.34 (t, J=6.8 Hz, 1H), 5.24-5.09 (m, 2H), 4.98 (s, 2H), 4.29 (s, 4H), 3.95-4.10 (m, 2H), 3.83-3.60 (m, 3H), 2.13 (s, 3H).

Synthesis of 4-((1-(2,3-dihydrobenzo[b][1,4]dioxin-6-yl)-2-oxo-1,2-dihydropyridin-3-yl)methoxy)-5-methyl-2-(pyridin-3-ylmethoxy)benzaldehyde

4

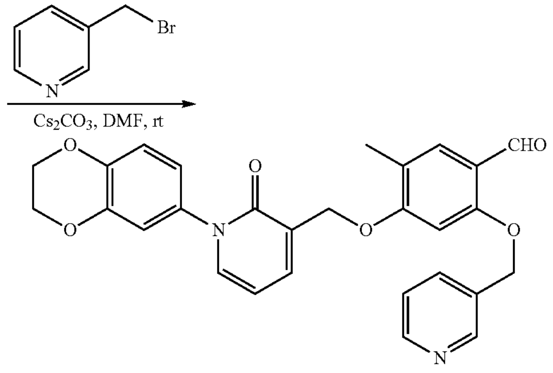

102

To a solution of 4-((1-(2,3-dihydrobenzo[b][1,4]dioxin-6-yl)-2-oxo-1,2-dihydropyridin-3-yl)methoxy)-2-hydroxy-5-methylbenzaldehyde (500 mg, 1.271 mmol, 1.0 eq.) in DMF (5 mL) was added 3-(bromomethyl)pyridine (262 mg, 1.525 mmol), $Cs_2CO_3$ (621 mg, 1.907 mmol). The resulting mixture was stirred at rt for overnight. The resulting mixture was dropwise added into 40 mL ice water, The suspension was filtered and washed with DMF to afford the titled compound as a white solid (500 mg, 81%). LC/MS: mass calcd. for $C_{28}H_{24}N_2O_6$: 484.5, found: 485.3 [M+H]+.

Synthesis of (4-((1-(2,3-dihydrobenzo[b][1,4]dioxin-6-yl)-2-oxo-1,2-dihydropyridin-3-yl)methoxy)-5-methyl-2-(pyridin-3-ylmethoxy)benzyl)-D-serine

103

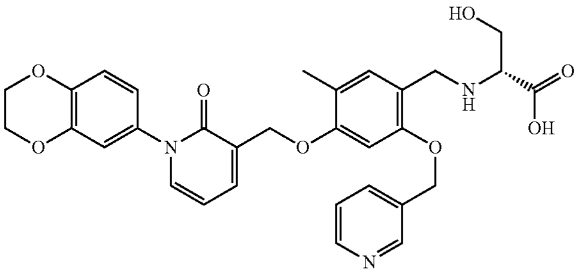

To a mixture of 4-((1-(2,3-dihydrobenzo[b][1,4]dioxin-6-yl)-2-oxo-1,2-dihydropyridin-3-yl)methoxy)-5-methyl-2-(pyridin-3-ylmethoxy)benzaldehyde (500 mg, 1.032 mmol, 1 eq) and D-Serine (433.8 mg, 4.128 mmol, 4 eq) in DMF (5 mL) was added acetic acid (6 mg, 0.103 mmol) and the mixture was stirred at rt for 30 min. Then $NaCNBH_3$ (227 mg, 3.612 mmol) was added and the mixture was heated at 80° C. for 3 h. The reaction was then cooled to rt, then dropwise added into water at 0° C. The solid obtained was purified by a reverse phase C18 column (0 to 60% $H_2O$ (0.5% TFA)/$CH_3CN$) to afford the titled compound as a white solid (159 mg, 33%). LC/MS: mass calcd. for $C_{31}H_{31}N_3O_8$: 573.21, found: 574.3[M+H]+. $^1H$ NMR (300 MHz, DMSO-$d_6$) δ 8.71 (d, J=2.2 Hz, 1H), 8.54 (dd, J=4.8, 1.6 Hz, 1H), 8.03-7.93 (m, 1H), 7.62 (dt, J=6.7, 3.0 Hz, 2H), 7.41 (dd, J=7.8, 4.8 Hz, 1H), 7.18 (s, 1H), 7.02-6.93 (m, 2H), 6.93-6.84 (m, 2H), 6.35 (t, J=6.8 Hz, 1H), 5.29-5.14 (m, 2H), 4.99 (s, 2H), 4.30 (s, 4H), 4.02-3.97 (m, 2H), 3.78-3.58 (m, 3H), 3.16 (d, J=6.0 Hz, 2H), 2.15 (s, 3H).

Synthesis of 5-chloro-4-((1-(2,3-dihydrobenzo[b][1,4]dioxin-6-yl)-2-oxo-1,2-dihydropyridin-3-yl)methoxy)-2-hydroxybenzaldehyde

3

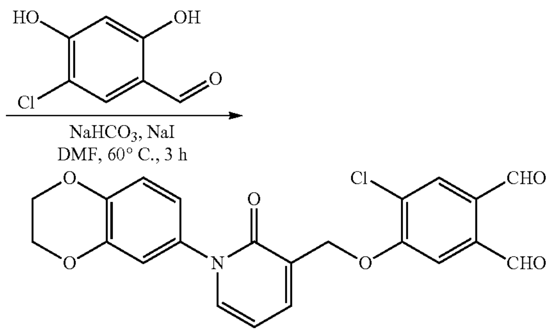

200

To a solution of 3-(chloromethyl)-1-(2,3-dihydrobenzo[b][1,4]dioxin-6-yl)pyridin-2(1H)-one (500 mg, 1.800 mmol, 1.0 eq.) in DMF (5 mL) was added 5-chloro-2,4-dihydroxybenzaldehyde (373 mg, 2.161 mmol, 1.2 eq.), $Na_2CO_3$ (227 mg, 2.701 mmol), NaI (135 mg, 0.90 mmol). The resulting mixture was stirred at 60° C. for 3 h. After cooling to rt, the mixture was dropwise added into 40 mL ice water, The suspension was filtered and washed with $CH_3OH$ to afford the 5-chloro-4-((1-(2,3-dihydrobenzo[b][1,4]dioxin-6-yl)-2-oxo-1,2-dihydropyridin-3-yl)methoxy)-2-hydroxybenzaldehyde as a white solid (500 mg, 67%). LC/MS: mass calcd. for $C_{21}H_{16}ClNO_6$: 413.81, found: 414.1 [M+H]+.

Synthesis of 3-((4-chloro-5-((1-(2,3-dihydrobenzo[b][1,4]dioxin-6-yl)-2-oxo-1,2-dihydropyridin-3-yl)methoxy)-2-formylphenoxy)methyl)benzonitrile

200

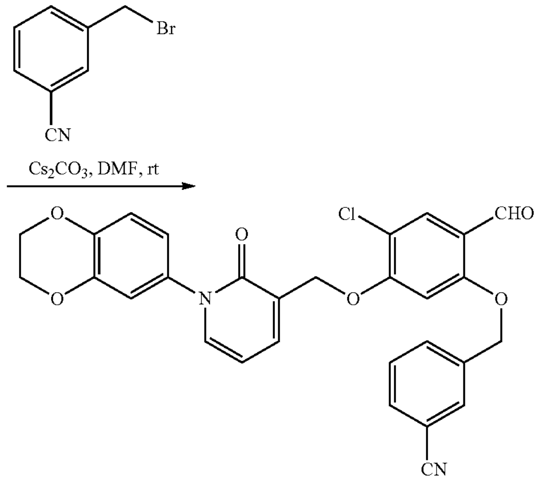

201

To a solution of 5-chloro-4-((1-(2,3-dihydrobenzo[b][1,4]dioxin-6-yl)-2-oxo-1,2-dihydropyridin-3-yl)methoxy)-2-hydroxybenzaldehyde (500 mg, 1.208 mmol) in DMF (5 mL) was added 3-(bromomethyl)benzonitrile (284 mg, 1.450 mmol), $Cs_2CO_3$ (590.5 mg, 1.812 mmol, 1.5 eq.). The resulting mixture was stirred at rt for overnight. The resulting mixture was dropwise added into ice water (40 mL), the suspension was filtered and washed with $CH_3OH$ to afford the titled compound as a white solid (400 mg, 63%). LC/MS: mass calcd. for $C_{29}H_{21}ClN_2O_6$: 528.94, found: 529.3 [M+H]+.

Synthesis of (5-chloro-2-((3-cyanobenzyl)oxy)-4-((1-(2,3-dihydrobenzo[b][1,4]dioxin-6-yl)-2-oxo-1,2-dihydropyridin-3-yl)methoxy)benzyl)-D-serine

201

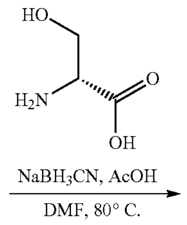

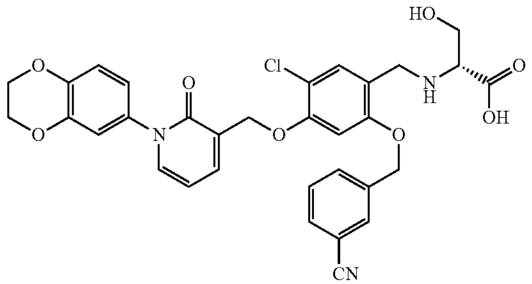

202

To a mixture of 3-((4-chloro-5-((1-(2,3-dihydrobenzo[b][1,4]dioxin-6-yl)-2-oxo-1,2-dihydropyridin-3-yl)methoxy)-2-formylphenoxy)methyl)benzonitrile (400 mg, 0.756 mmol) and D-Serine (318 mg, 3.025 mmol) in DMF (5 mL) was added acetic acid (4.5 mg, 0.076 mmol) and the mixture was stirred at rt for 30 min. Then $NaCNBH_3$ (166 mg, 2.65 mmol) was added and the mixture was heated to 80° C. for 3 h. The reaction was cooled to rt, and the mixture was added dropwise into water at 0° C., The crude was purified by reverse phase column chromatography (C18 column, 0 to 60% $H_2O$ (0.5% TFA)/$CH_3CN$) to afford the titled compound as a white solid (159 mg, 33%). LC/MS: mass calcd. for $C_{32}H_{28}ClN_3O_8$: 617.16, found: 618.2[M+H]+. $^1H$ NMR (300 MHz, DMSO-$d_6$) δ 7.95 (d, J=1.7 Hz, 1H), 7.90-7.77 (m, 2H), 7.77-7.54 (m, 3H), 7.50 (s, 1H), 7.05 (s, 1H), 6.97 (dd, J=5.5, 3.1 Hz, 2H), 6.87 (dd, J=8.6, 2.5 Hz, 1H), 6.36 (t, J=6.8 Hz, 1H), 5.33-5.17 (m, 2H), 5.05 (s, 2H), 4.28 (s, 4H), 3.96 (s, 2H), 3.60-3.76 (m, 4H), 3.18 (t, J=5.4 Hz, 1H).

Synthesis of (S)-3-((4-chloro-5-((1-(2,3-dihydrobenzo[b][1,4]dioxin-6-yl)-2-oxo-1,2-dihydropyridin-3-yl)methoxy)-2-((((5-oxopyrrolidin-2-yl)methyl)amino)methyl)phenoxy)methyl)benzonitrile

201

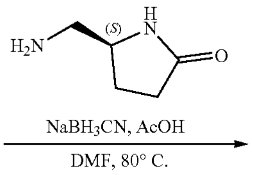

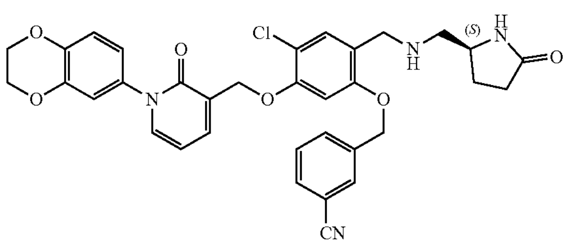

205

To a mixture of 3-((4-chloro-5-((1-(2,3-dihydrobenzo[b][1,4]dioxin-6-yl)-2-oxo-1,2-dihydropyridin-3-yl)methoxy)-2-formylphenoxy)methyl)benzonitrile (400 mg, 0.756 mmol, 1 eq) and (S)-5-AMINOMETHYL-PYRROLIDIN-2-ONE (345 mg, 3.025 mmol, 4 eq) in DMF (5 ml) was added acetic acid (4.5 mg, 0.076 mmol) and the mixture was stirred at rt for 30 min. Then $NaCNBH_3$ (166 mg, 2.65 mmol) was added and the mixture was heated at 80° C. for 3 h. The reaction was then cooled to rt. The mixture was dropwise added in water at 0° C. The precipitate was filtered and purified by reverse phase column chromatography (C18 column, 0 to 60% $H_2O$ (0.5% TFA)/$CH_3CN$). After lyophilization, the titled compound was afforded as a white solid (78.2 mg, 13% yield). LC/MS: mass calcd. for $C_{34}H_{31}ClN_4O_6$: 627.086, found: 627.20 [M+H]+. 1H NMR (300 MHz, DMSO-d6) δ (ppm): 8.47-8.89 (m, 2H), 7.93 (s, 1H), 7.74-7.91 (m, 2H), 7.41-7.74 (m, 5H), 7.21 (s, 1H), 6.91-6.99 (m, 2H), 6.31-6.42 (m, 1H), 5.27 (s, 2H), 5.09 (s, 2H), 4.29 (s, 4H), 4.17 (s, 2H), 3.75-3.91 (m, 1H), 2.83-3.09 (m, 2H), 2.05-2.21 (m, 3H), 1.68-1.79 (in, 1H)

The following compounds were synthesized using an analogous procedure as in the preparation of compound 202.

| # | STRUCTURE | Exact Mass | LC-MS (M + H) | $^1$H NMR |
|---|---|---|---|---|
| 203 | 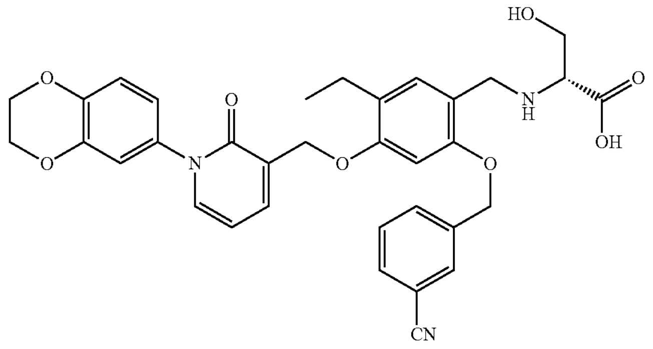 203 | 611.23 | 612.2 | $^1$H NMR (300 MHz, DMSO-$d_6$) δ 7.96 (s, 1H), 7.83 (dd, J = 24.0, 9.0 Hz, 4H), 7.65-7.52 (m, 3H), 7.18 (d, J = 3.5 Hz, 1H), 6.99-6.88 (m, 2H), 6.88-6.78 (m, 2H), 6.33 (t, J = 6.9 Hz, 1H), 5.20 (d, J = 4.0 Hz, 3H), 4.95 (s, 1H), 4.27 (s, 4H), 4.11-3.94 (m, 2H), 3.73 (dd, J = 11.3, 4.6 Hz, 1H), 3.62 (dd, J = 11.3, 6.7 Hz, 2H), 3.16 (d, J = 6.9 Hz, 1H), 2.54 (dd, J = 7.5, 2.5 Hz, 3H), 1.11 (td, J = 7.5, 2.9 Hz, 3H) |
| 204 | 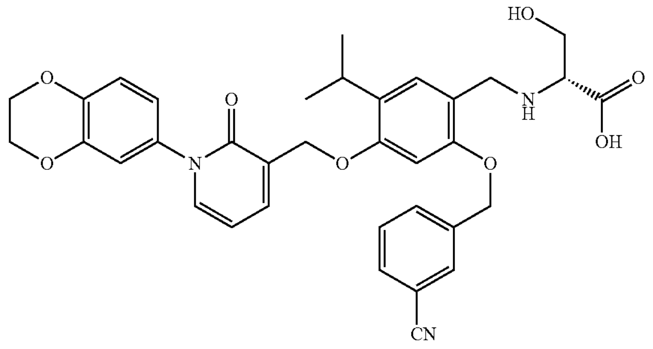 204 | 625.24 | 624.3 (M − H) | $^1$H NMR (300 MHz, DMSO-$d_6$) δ 7.96 (s, 1H), 7.91-7.70 (m, 3H), 7.58 (dd, J = 9.2, 6.6 Hz, 3H), 7.25 (d, J = 3.9 Hz, 1H), 6.99-6.91 (m, 2H), 6.83 (td, J = 7.7, 6.9, 3.9 Hz, 2H), 6.33 (t, J = 6.8 Hz, 1H), 5.20 (d, J = 3.1 Hz, 2H), 4.95 (s, 2H), 4.27 (s, 4H), 4.13-3.96 (m, 2H), 3.73 (dd, J = 11.2, 4.5 Hz, 1H), 3.63 (dd, J = 11.4, 6.6 Hz, 2H), 3.21 (td, J = 13.8, 6.7 Hz, 3H), 1.14 (dd, J = 7.0, 3.2 Hz, 6H). |

The following compounds were prepared using a procedure analogous to those described in the preparation of compound 10.

| # | STRUCTURE | Exact Mass | LC-MS (M + H) | $^1$H NMR |
|---|---|---|---|---|
| 11 | 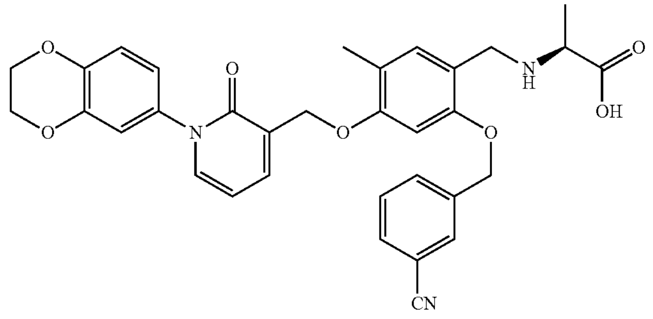 [SMILES: Cc1cc(CN[C@@H](C)C(=O)O)c(OCc2cccc(C#N)c2)cc1OCc1cccn(-c2ccc3c(c2)OCCO3)c1=O] | 581.62 | 582.2 | $^1$H NMR (300 MHz, DMSO-$d_6$) δ 8.98 (s, 1H), 7.95 (t, J = 1.7 Hz, 1H), 7.87-7.75 (m, 2H), 7.65-7.53 (m, 3H), 7.22 (s, 1H), 7.00-6.90 (m, 2H), 6.90-6.79 (m, 2H), 6.33 (t, J = 6.8 Hz, 1H), 5.29-5.14 (m, 2H), 4.98 (s, 2H), 4.27 (s, 4H), 4.11 (s, 2H), 3.97-3.86 (m, 1H), 2.14 (s, 3H), 1.42 (d, J = 7.1 Hz, 3H). |

-continued

| # | STRUCTURE | Exact Mass | LC-MS (M + H) | $^1$H NMR |
|---|---|---|---|---|
| 12 | 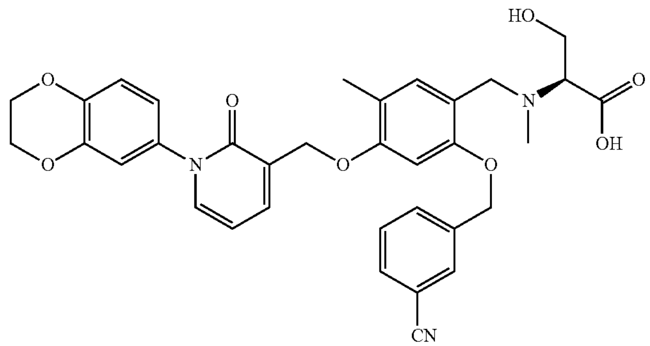 [SMILES: Cc1cc(CN(C)[C@@H](CO)C(=O)O)c(OCc2cccc(C#N)c2)cc1OCc1cccn(-c2ccc3c(c2)OCCO3)c1=O] | 611.64 | 612.2 | $^1$H NMR (300 MHz, DMSO-$d_6$) δ 7.91 (d, J = 1.9 Hz, 1H), 7.89-7.73 (m, 3H), 7.58 (t, J = 7.7 Hz, 2H), 7.13 (s, 1H), 6.95 (dd, J = 5.5, 3.1 Hz, 2H), 6.89-6.77 (m, 2H), 6.33 (t, J = 6.8 Hz, 1H), 5.18 (s, 2H), 4.94 (s, 2H), 4.28 (s, 4H), 3.99-3.74 (m, 4H), 2.80 (d, J = 7.2 Hz, 2H), 2.43 (s, 3H), 2.12 (s, J = 2.5 Hz, 3H). |

Synthesis of 5-((4-chloro-5-((1-(2,3-dihydrobenzo[b][1,4]dioxin-6-yl)-2-oxo-1,2-dihydropyridin-3-yl)methoxy)-2-formylphenoxy)methyl)nicotinonitrile

200

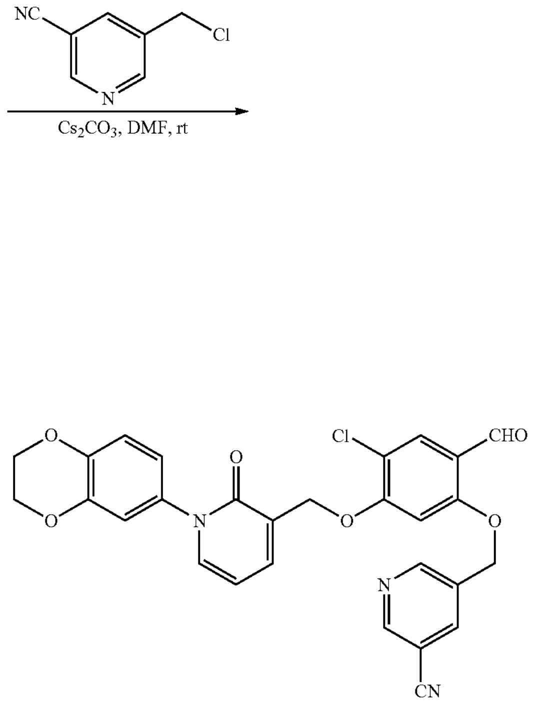

206

To a solution of 5-(chloromethyl)nicotinonitrile (350 mg, 2.3 mmol) in DMF (4 mL) was added 5-chloro-4-((1-(2,3-dihydrobenzo[b][1,4]dioxin-6-yl)-2-oxo-1,2-dihydropyridin-3-yl)methoxy)-2-hydroxybenzaldehyde (790 mg, 1.9 mmol), Cesium carbonate (935 mg, 2.9 mmol). The resulting mixture was stirred at rt for overnight. The resulting mixture was dropwise added into 30 mL ice water. The suspension was filtered and washed with MeOH to afford the titled compound as white solid (340 mg, 34.5% yield) LC/MS: mass calcd. for $C_{28}H_{20}ClN_3O_6$: 529.928, found: 530.40 [M+H]+.

Synthesis of (5-chloro-2-((5-cyanopyridin-3-yl)methoxy)-4-((1-(2,3-dihydrobenzo[b][1,4]dioxin-6-yl)-2-oxo-1,2-dihydropyridin-3-yl)methoxy)benzyl)-D-serine

206

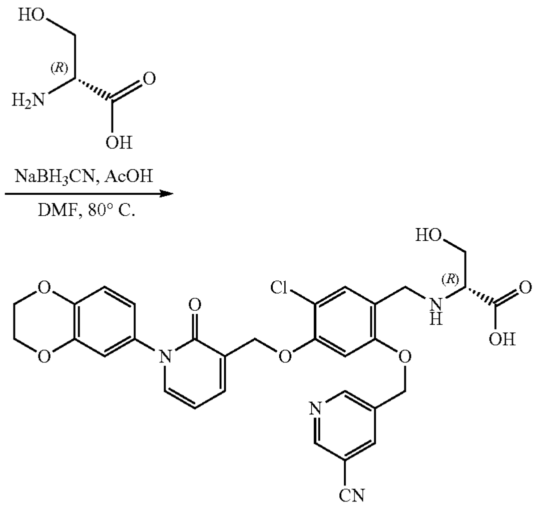

207

To a mixture of 5-((4-chloro-5-((1-(2,3-dihydrobenzo[b][1,4]dioxin-6-yl)-2-oxo-1,2-dihydropyridin-3-yl)methoxy)-2-formylphenoxy)methyl)nicotinonitrile (300 mg, 0.57 mmol) and D-Serine (240 mg, 2.3 mmol) in DMF (4 mL) was added acetic acid (3.4 mg, 0.057 mmol) and the mixture was stirred at rt for 30 min. Then $NaCNBH_3$ (125 mg, 2 mmol) was added and the mixture was heated to 80° C. for 3 h. The reaction was cooled to rt, and the mixture was added dropwise into water at 0° C. The precipitate was filtered and purified by reverse phase column chromatography (C18 column, 0 to 60% $H_2O$ (0.5% TFA)/$CH_3CN$) to afford the titled compound as a white solid (54 mg, 15%). LC/MS: mass calcd. for $C_{31}H_{27}ClN_4O_8$: 618.021, found: 619.10 [M+H]+. $^1$H NMR (300 MHz, DMSO-d6) δ (ppm): 9.01-9.05 (m, 1H), 8.96-8.99 (m, 1H), 8.39-8.46 (m, 1H), 7.65-7.71 (m, 2H), 7.59 (s, 1H), 7.12 (s, 1H), 6.91-7.01 (m, 2H), 6.82-6.91 (m, 1H), 6.38 (t, J=6.9 Hz, 1H), 5.51-6.62 (m, 1H), 5.30 (s, 2H), 5.11 (s, 2H), 4.14-4.55 (m, 6H), 3.91 (s, 1H), 3.85 (s, 2H).

Synthesis of 2-((5-(1H-1,2,3-triazol-1-yl)pyridin-3-yl)methoxy)-5-chloro-4-((1-(2,3-dihydrobenzo[b][1,4]dioxin-6-yl)-2-oxo-1,2-dihydropyridin-3-yl)methoxy)benzaldehyde 200
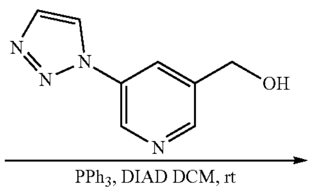

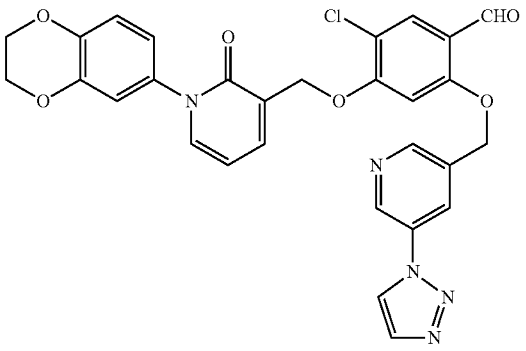

208

To a mixture of (5-(1H-1,2,3-triazol-1-yl)pyridin-3-yl) methanol [1646287-85-5] (180 mg, 1 mmol), 5-chloro-4-((1-(2,3-dihydrobenzo[b][1,4]dioxin-6-yl)-2-oxo-1,2-dihydropyridin-3-yl)methoxy)-2-hydroxybenzaldehyde (422, 1 mmol) and triphenylphosphine (400 mg, 1.5 mmol,) in DCM (4 ml) was added diisopropyl azodicarboxylate (310 mg, 1.5 mmol) at 0° C. under N2. The mixture was stirred at rt for 18 hours. The mixture was concentrated under reduced pressure. The residue obtained was purified by reverse C18 column (0-60% $H_2O$ (0.5% TFA)/ACN) to afford titled compound as white solid (150 mg, 26% yield). LC/MS: mass calcd. for $C_{29}H_{22}ClN_5O_6$: 571.968, found: 572.25[M+H]+.

Synthesis of ((2-((5-(1H-1,2,3-triazol-1-yl)pyridin-3-yl)methoxy)-5-chloro-4-((1-(2,3-dihydrobenzo[b][1,4]dioxin-6-yl)-2-oxo-1,2-dihydropyridin-3-yl)methoxy)benzyl)-D-serine 208
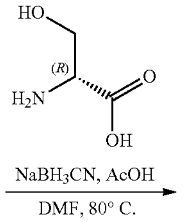

-continued

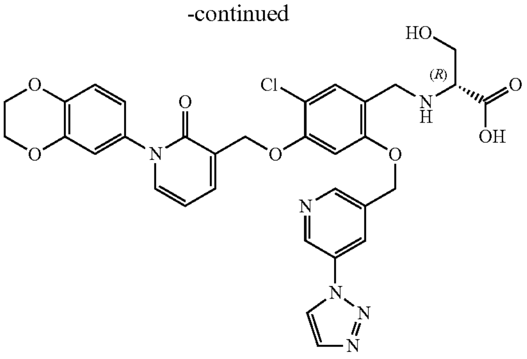

209

To a mixture of 2-((5-(1H-1,2,3-triazol-1-yl)pyridin-3-yl) methoxy)-5-chloro-4-((1-(2,3-dihydrobenzo[b][1,4]dioxin-6-yl)-2-oxo-1,2-dihydropyridin-3-yl)methoxy)benzaldehyde (150 mg, 0.26 mmol) and D-Serine (110 mg, 1 mmol) in DMF (4 ml) was added acetic acid 1 (1.6 mg, 0.026 mmol) and the mixture was stirred at rt for 30 min. Then $NaCNBH_3$ (60 mg, 0.9 mmol) was added and the mixture was heated at 80° C. for 3 h. The reaction was then cooled to rt. The mixture was dropwise added in water at 0° C. The precipitate was filtered and then purified by reverse phase column chromatography (C18 column, 0 to 60% $H_2O$ (0.5% TFA)/$CH_3CN$). After lyophilization, the titled compound was afforded as a white solid (28.6 mg, 16% yield) LC/MS: mass calcd. for $C_{32}H_{29}ClN_6O_8$: 660.17, found: 661.15 [M+H]+. $^1H$ NMR (300 MHz, DMSO-d6) d (ppm): 9.41 (s, 1H), 9.15-9.21 (m, 1H), 8.72-8.76 (m, 1H), 8.60-8.66 (m, 1H), 8.00 (s, 1H), 7.58-7.68 (m, 2H), 7.54 (s, 1H), 7.12 (s, 1H), 6.91-7.01 (m, 2H), 6.83-6.91 (m, 1H), 6.34 (t, J=6.8 Hz, 1H), 5.33 (s, 2H), 5.08 (s, 2H), 4.26 (s, 4H), 3.89-4.08 (m, 3H), 3.03-3.13 (m, 2H).

Example 2: PD-1/PD-L1 Biochemical Protein-Protein Interaction

Compounds were tested in protein-protein interaction assay to determine if they can specifically block the interaction between the extracellular domains of PD-1/PD-L1. Binding of the protein pairs is measured using a bead based amplified luminescent proximity homogeneous assay (ALPHA) platform. Binding of each protein pair results in proximity of the donor and acceptor beads which leads to an increase in ALPHA signal. Assays are performed in 50 mM Tris (pH 7.4), 0.0015% Triton X-100, 0.1% BSA. Final protein concentration in the assays were 5 nM (His tagged PD-L1), 5 nM (biotinylated PD-1), 10 μg/ml ALPHA assay acceptor beads, 10 μg/ml ALPHA assay donor beads. After an assay reaction time of 2 hours at 25° C., binding was measured. The specificity of the binding was determined by testing the compounds in an assay with an irrelevant protein that is both His tagged and biotinylated. The final protein concentration used in the assay was 5 nM, 10 μg/ml ALPHA assay acceptor beads, 10 μg/ml ALPHA assay donor beads. After an assay reaction time of 2 hours at 25° C., binding was measured. $IC_{50}$ values were calculated from the fit of the dose-response curves to a four-parameter equation.

The specificity of the binding was determined by testing the compounds in an assay with an irrelevant protein that is both His tagged and biotinylated (ErbB3/her3). The final protein concentration used in the assay was 5 nM, 10 μg/mL ALPHA assay acceptor beads, 10 μg/mL ALPHA assay donor beads. After an assay reaction time of 2 hours at 25° C., binding was measured. $IC_{50}$ values were calculated from the fit of the dose-response curves to a four-parameter equation. Compounds were specific if they show $EC_{50}$>25 μM in this assay or that the stimulation index compared to the PD-1/PD-L1 interaction was greater than three.

TABLE 1a

| Compound Activity | |
|---|---|
| Compound Number | ALPHA-LISA $IC_{50}$ (μM) |
| 7 | 1.1 |
| 8 | 3.4 |
| 10 | 1.2 |
| 11 | 3.9 |
| 12 | 1.6 |
| 101 | 3.0 |
| 103 | 1.0 |
| 202 | 0.2 |
| 203 | 2.7 |
| 204 | 3.6 |

TABLE 1b

| Compound Activity | |
|---|---|
| Compound Number | ALPHA-LISA $IC_{50}$ (μM) |
| 205 | 0.36 |
| 207 | 0.32 |
| 209 | 0.55 |

Example 3: PD-1/PD-L1 NFAT Reporter Assay

Compounds were tested in functional co-culture reporter assay in which TCR-mediated NFAT activity is inhibited by the engagement of PD-1 with PD-L1. Blocking the PD-1/PD-L1 interaction impairs PD-1 mediated blunting of TCR signaling and significantly increase NFAT-mediated transcription of luciferase. CHO cells expressing surface-bound anti-CD3 antibodies and PD-L1 (artificial antigen-presenting cells, aAPC-PD-L1) were mixed with Jurkat cells overexpressing PD-1 and expressing a luciferase construct under NFAT control in RPMU assay medium with 1% FBS and immediately seeded on plates containing the compounds. The co-culture is then incubated for 20 hours at 37° C., 5% $CO_2$. Luciferase activity is assessed by adding the Bio-Glo reagent and measuring luminescence with a plate reader. Data are reported as least effective concentrations (LEC). LEC values are calculated from the fit of the dose response curves to the mean of the cell control plus three times the standard deviation.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula (I), (I)

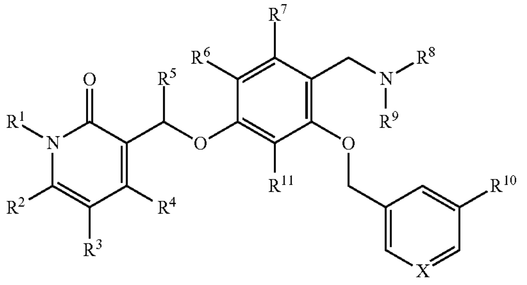

or a stereoisomer or tautomeric form thereof, or a pharmaceutically acceptable salt thereof, wherein $R^1$ is a ring optionally substituted with one or more substituents selected from the group consisting of halogen, CN, $C_{1-6}$ alkyl, $C_{1-6}$ haloalkyl, $C_{3-6}$ cycloalkyl, $C_{1-6}$ heteroalkyl, $NR^xR^y$, $NR^xC(=O)R^y$, $NR^xCO_2R^y$, $NR^xC(=O)NR^xR^y$, $OC(=O)NR^xR^y$, O-(6 to 10-membered aryl), O-(5 to 10-membered heteroaryl), and a ring;

$R^2$, $R^3$, $R^4$, $R^5$, $R^6$, $R^7$ and $R^{11}$ are independently selected from the group consisting of H, halogen, $C_{1-4}$ alkyl and $C_{1-4}$ alkyl substituted with one or more F;

$R^8$ and $R^9$ are independently selected from the group consisting of H, $C_{1-6}$ alkyl and $C_{1-6}$ heteroalkyl, wherein each of the $C_{1-6}$ alkyl and $C_{1-6}$ heteroalkyl is optionally substituted with one or more substituents selected from the group consisting of $C_{1-4}$ alkyl, OH, $OCH_3$, $—CO_2H$, $—CO_2C_{1-4}$ alkyl, $C_{3-6}$ heterocycle, aryl and heteroaryl, wherein the $C_{3-6}$ heterocycle is optionally substituted with one or more substituent selected from the group consisting of oxo, OH and $CO_2H$;

with the proviso that $R^8$ and $R^9$ are not both H;

or $R^8$ and $R^9$ are connected together to form a $C_{3-6}$heterocycle optionally substituted with one or more substituents selected from the group consisting of $C_{1-6}$ alkyl, oxo, OH and $CO_2H$;

$R^{10}$ is selected from the group consisting of H, CN, halogen, $C_{1-6}$ alkyl, $OC_{1-6}$ alkyl, $C_{1-6}$ alkyl-$CO_2H$, $C_{1-6}$ alkyl-$CO_2$—$C_{1-6}$ alkyl, $C_{1-6}$ alkyl-C(O)$NH_2$, $C_{1-6}$ alkyl-CO—$NHC_{1-6}$ alkyl, $C_{1-6}$ alkyl-C(O)N($C_{1-6}$ alkyl)$_2$, $C(=O)NR^xR^y$, $SO_2$—$C_{1-6}$ alkyl, aryl and heteroaryl;

wherein the aryl and heteroaryl are optionally substituted with one or more substituents selected from the group consisting of CN, halogen, $C_{1-6}$ alkyl, $OC_{1-6}$ alkyl, $C_{1-6}$ alkyl-$CO_2H$, $C_{1-6}$ alkyl-$CO_2$—$C_{1-6}$ alkyl, $C_{1-6}$ alkyl-C(O)$NH_2$, $C_{1-6}$ alkyl-CO—$NHC_{1-6}$ alkyl, $C_{1-6}$ alkyl-C(O)N($C_{1-6}$ alkyl)$_2$, $C(=O)NR^xR^y$ and $SO_2$—$C_{1-6}$ alkyl;

X is N or $CR^{12}$;

$R^{12}$ is selected from the group consisting of H, F, Cl, CN, $C(=O)NR^xR^y$, aryl and heteroaryl, wherein the aryl and heteroaryl are optionally substituted with one or more substituents selected from the group consisting of CN, halogen, $C_{1-6}$ alkyl, $OC_{1-6}$ alkyl, $C_{1-6}$ alkyl-$CO_2H$, $C_{1-6}$ alkyl-$CO_2$—$C_{1-6}$ alkyl, $C_{1-6}$ alkyl-C(O)$NH_2$, $C_{1-6}$ alkyl-CO—$NHC_{1-6}$ alkyl, $C_{1-6}$ alkyl-C(O)N($C_{1-6}$ alkyl)$_2$, C(═O)$NR^xR^y$ and $SO_2$—$C_{1-6}$ alkyl; and $R^x$ and $R^y$ are independently selected from the group consisting of H and $C_{1-6}$ alkyl.

2. The compound of claim 1, wherein $R^2$, $R^3$, $R^4$, $R^5$, $R^6$, $R^7$ and $R^{11}$ are independently selected from the group consisting of H and $C_{1-4}$ alkyl.

3. The compound of claim 1, wherein $R^6$ is $C_{1-4}$ alkyl or Cl.

4. The compound of claim 1, wherein $R^6$ is Cl, $R^2$, $R^3$, $R^4$, $R^5$, $R^7$ and $R^{11}$ are H.

5. The compound of claim 1, wherein $R^1$ is formula, (g-1)

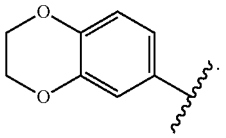

6. The compound of claim 1, wherein $R^8$ is H and $R^9$ is $C_{1-6}$ alkyl substituted with OH and $CO_2H$.

7. The compound of claim 1, wherein $R^8$ and $R^9$ are connected together to form a $C_{3-6}$ heterocycle substituted with OH and $CO_2H$.

8. The compound of claim 7, wherein the $C_{3-6}$ heterocycle is pyrrolidine.

9. The compound of claim 1, wherein $R^{10}$ is CN and X is N.

10. The compound of claim 1, wherein $R^{10}$ is H and X is N.

11. The compound of claim 1, wherein the $IC_{50}$ is equal or less than 5 μM in amplified luminescent proximity homogeneous assay (ALPHA)-LISA.

12. A compound selected from the group consisting of compound 7

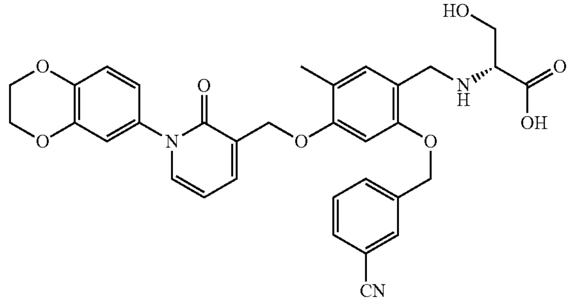

-continued compound 8

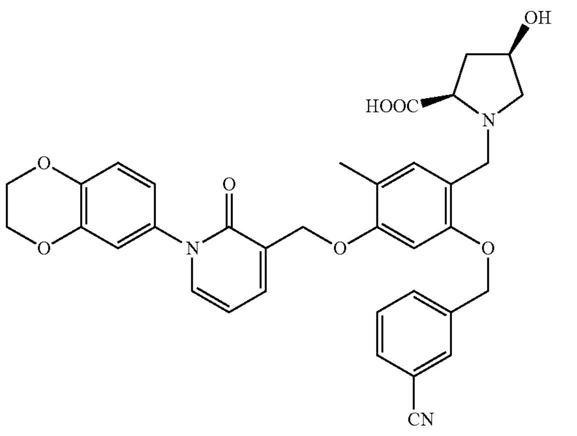

compound 9

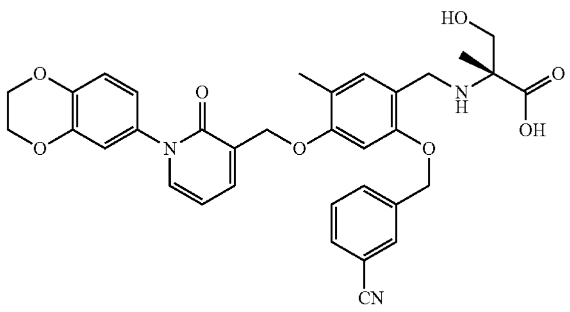

compound 10

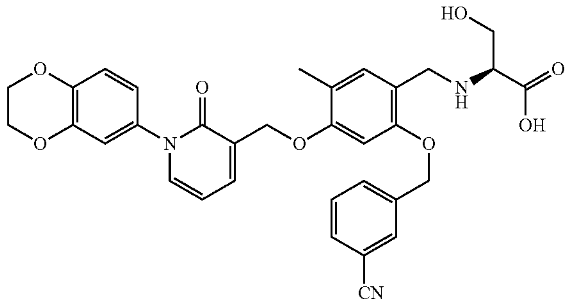

compound 11

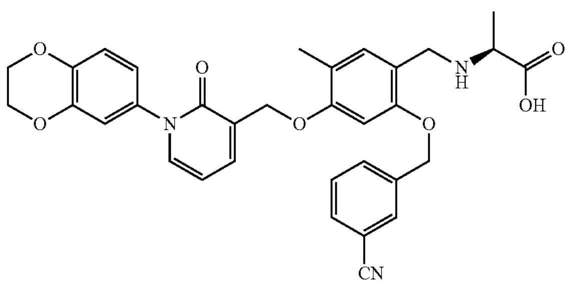

-continued compound 12

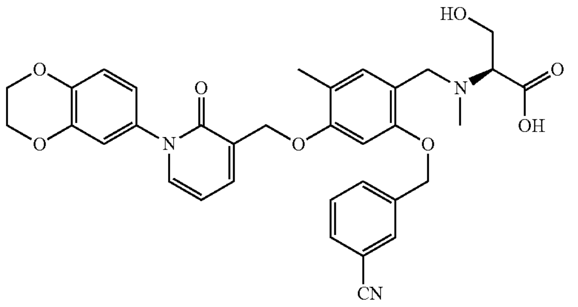

compound 101

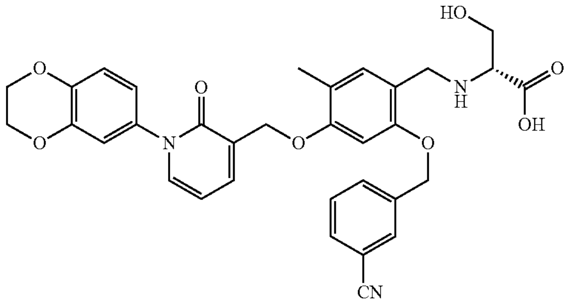

compound 103

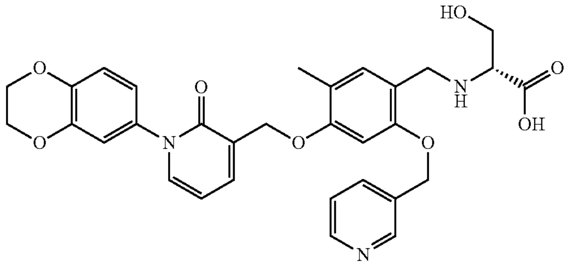

compound 202

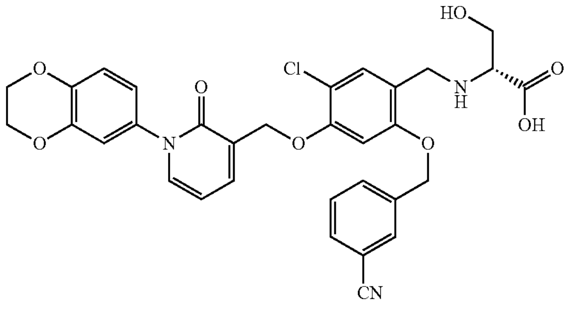

compound 203

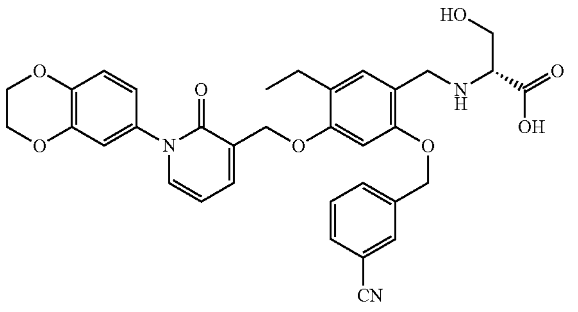

-continued compound 204

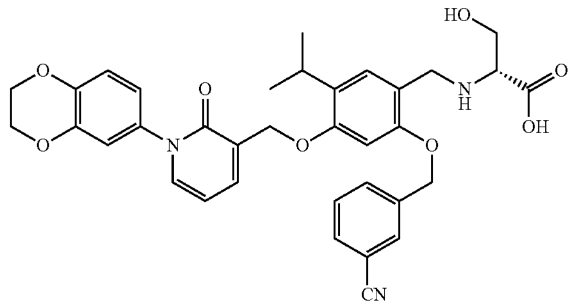

or a stereoisomer or tautomeric form thereof, or a pharmaceutically acceptable salt thereof.

13. A compound selected from the group consisting of compound 205

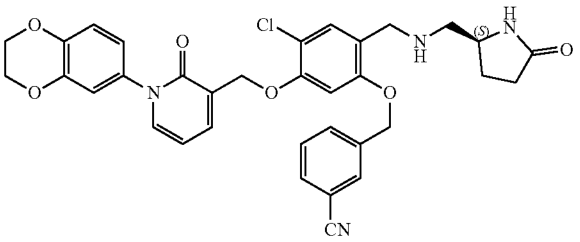

compound 207

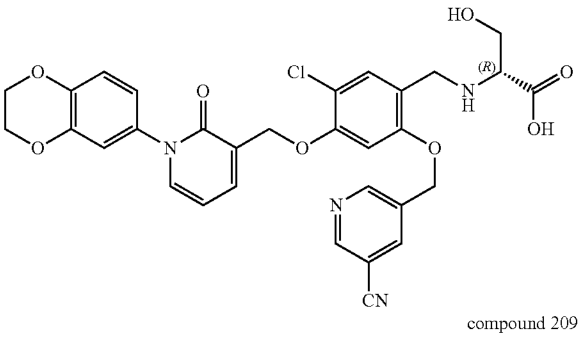

compound 209

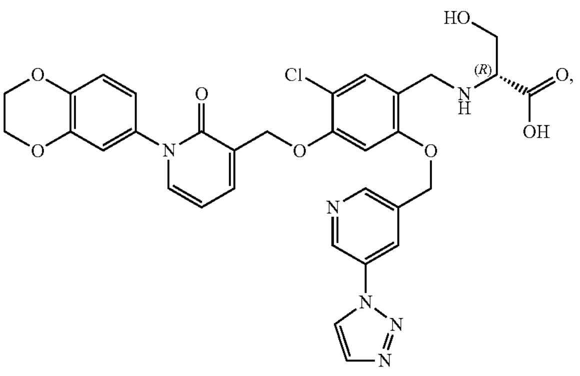

or a stereoisomer or tautomeric form thereof, or a pharmaceutically acceptable salt thereof.

14. A pharmaceutical composition, comprising the compound or the pharmaceutically acceptable salt of claim 1 and at least one pharmaceutically acceptable carrier.

15. A method of inhibiting PD-L1 in a subject in need thereof, comprising administering to the subject an effective amount of the compound or the pharmaceutically acceptable salt of claim 1.

16. A process for preparing a compound of Formula (I) according to claim 1, comprising reacting a compound of formula (II)

(II)

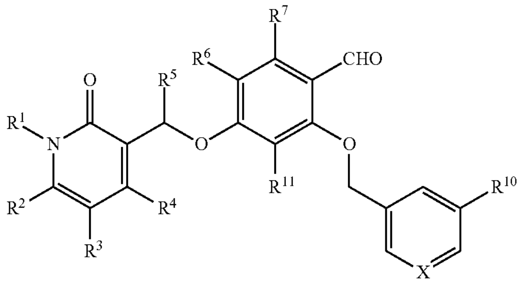

with an amine of formula (III), (III)

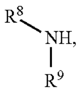

in the presence of sodium cyanoborohydride, wherein $R^1$, $R^2$, $R^3$, $R^4$, $R^5$, $R^6$, $R^7$, $R^8$, $R^9$, $R^{10}$, $R^{11}$ and X are defined as in claim 1.

* * * * *